United States Patent [19]

Certa

[11] Patent Number: 5,061,788

[45] Date of Patent: Oct. 29, 1991

[54] RECOMBINANT MALARIAL POLYPEPTIDES

[75] Inventor: Ulrich Certa, Allschwil, Switzerland

[73] Assignee: Hoffmann-La Roche Inc., Nutley, N.J.

[21] Appl. No.: 237,126

[22] Filed: Aug. 29, 1988

[30] Foreign Application Priority Data

Sep. 8, 1987 [CH] Switzerland .......................... 3486/87

[51] Int. Cl.$^5$ ........................ C07K 13/00; C12N 15/09
[52] U.S. Cl. .................................... 530/350; 530/395; 435/172.3
[58] Field of Search .............................. 530/350, 395; 435/172.3

[56] References Cited

FOREIGN PATENT DOCUMENTS

| 75245/87 | 6/1987 | Australia . |
| 283829 | 3/1988 | European Pat. Off. . |
| 88/1775 | 3/1988 | South Africa . |
| WO86/04922 | 8/1986 | World Int. Prop. O. . |

OTHER PUBLICATIONS

Villarejo et al., J. Bacteriol. 120:466–474 (1974).
Young et al., Proc. Natl. Acad. Sci. U.S.A. 80:1194–1198 (1983).
Sulkowski, Trends on Biotechnology 3:1–7 (1985).
Trager et al., Science 193:673–675 (1976).
Ponnudurai et al., Trans. R. Soc. Trop. Med. Hyg. 76:812–818 (1982).
Mazier et al., Science 227:440–442 (1985).
Weber et al., Nucleic Acids Res. 14:3311–3323 (1986).
Cheung et al., EMBO J. 4:1007–1011 (1985).
McGarvey et al., Proc. Natl. Acad. Sci. U.S.A. 81:3690–3694 (1984).

*Primary Examiner*—Nathan M. Nutter
*Attorney, Agent, or Firm*—George M. Gould; William H. Epstein; Patricia S. Rocha

[57] ABSTRACT

The invention provides polypeptides which correspond in at least one specific epitope with *Plasmodium falciparum* merozoite antigen having a molecular weight of about 41,000 Daltons, and a process for their production. The invention further provides immunogenic compositions which contain such a polypeptide and a suitable adjuvant, a DNA sequence which codes for such a polypeptide, replicable microbial vectors which contain such a DNA sequence, microorganisms which contain such a replicable vector and antibodies against a polypeptide of the invention. The invention still further provides processes for the production of the immunogenic compositions, the microorganisms and the antibodies and for the use of the polypeptides and the immunogenic compositions for the immunization of mammals against malaria.

9 Claims, 24 Drawing Sheets

FIG. 2a

```
             10         20         30         40         50
              |          |          |          |          |
   1 CTCGAGAAAT CATAAAAAAT TTATTTGCTT TGTGAGCGGA TAACAATTAT
  51 AATAGATTCA ATTGTGAGCG ATAACAATT TCACACAGAA TTCATTAAAG
 101 AGGAGAAATT AACTATGAGA GGATCCGGCA TCATGGTTCG ACCATTGAAC
 151 TGCATCGTCG CCGTGTCCCA AAATATGGGG ATTGGCAAGA ACGGAGACCT
 201 ACCCTGGCCT CCGCTCAGGA ACGAGTTCAA GTACTTCCAA AGAATGACCA
 251 CAACCTCTTC AGTGGAAGGT AAACAGAATC TGGTGATTAT GGGTAGGAAA
 301 ACCTGGTTCT CCATTCCTGA GAAGAATCGA CCTTTAAAGG ACAGAATTAA
 351 TATAGTTCTC AGTAGAGAAC TCAAAGAACC ACCACGAGGA GCTCATTTTC
 401 TTGCCAAAAG TTTGGATGAT GCCTTAAGAC TTATTGAACA ACCGGAATTG
 451 GCAAGTAAAG TAGACATGGT TTGGATAGTC GGAGGCAGTT CTGTTTACCA
 501 GGAAGCCATG AATCAACCAG GCCACCTTAG ACTCTTTGTG ACAAGGATCA
 551 TGCAGGAATT TGAAAGTGAC ACGTTTTTCC CAGAAATTGA TTTGGGGAAA
 601 TATAAACTTC TCCCAGAATA CCCAGGCGTC CTCTCTGAGG TCCAGGAGGA
 651 AAAAGGCATC AAGTATAAGT TTGAAGTCTA CGAGAAGAAA GGTTCCAGAT
 701 CTGTTAACCT AGTTTAACAG GAAGATGCTT TCAAGTTCTC TGCTCCCCTC
 751 CTAAAGCTAT GCATTTTTAT AAGACCATGG GACTTTTGCT GGCTTTAGAT
 801 CCGGCCAAGC TTGGACTCCT GTTGATAGAT CCAGTAATGA CCTCAGAACT
 851 CCATCTGGAT TTGTTCAGAA CGCTCGGTTG CCGCCGGGCG TTTTTTATTG
 901 GTGAGAATCC AAGCTAGCTT GGCGAGATTT TCAGGAGCTA AGGAAGCTAA
 951 AATGGAGAAA AAAATCACTG GATATACCAC CGTTGATATA TCCCAATGGC
1001 ATCGTAAAGA ACATTTTGAG GCATTTCAGT CAGTTGCTCA ATGTACCTAT
1051 AACCAGACCG TTCAGCTGGA TATTACGGCC TTTTTAAAGA CCGTAAAGAA
1101 AAATAAGCAC AAGTTTTATC CGGCCTTTAT TCACATTCTT GCCCGCCTGA
1151 TGAATGCTCA TCCGGAATTT CGTATGGCAA TGAAAGACGG TGAGCTGGTG
```

FIG. 2b

```
1201 ATATGGGATA GTGTTCACCC TTGTTACACC GTTTTCCATG AGCAAACTGA
1251 AACGTTTTCA TCGCTCTGGA GTGAATACCA CGACGATTTC CGGCAGTTTC
1301 TACACATATA TTCGCAAGAT GTGGCGTGTT ACGGTGAAAA CCTGGCCTAT
1351 TTCCCTAAAG GGTTTATTGA GAATATGTTT TTCGTCTCAG CCAATCCCTG
1401 GGTGAGTTTC ACCAGTTTTG ATTTAAACGT GGCCAATATG GACAACTTCT
1451 TCGCCCCCGT TTTCACCATG GGCAAATATT ATACGCAAGG CGACAAGGTG
1501 CTGATGCCGC TGGCGATTCA GGTTCATCAT GCCGTCTGTG ATGGCTTCCA
1551 TGTCGGCAGA ATGCTTAATG AATTACAACA GTACTGCGAT GAGTGGCAGG
1601 GCGGGGCGTA ATTTTTTTAA GGCAGTTATT GGTGCCCTTA AACGCCTGGG
1651 GTAATGACTC TCTAGCTTGA GGCATCAAAT AAAACGAAAG GCTCAGTCGA
1701 AAGACTGGGC CTTTCGTTTT ATCTGTTGTT TGTCGGTGAA CGCTCTCCTG
1751 AGTAGGACAA ATCCGCCGCT CTAGAGCTGC CTCGCGCGTT TCGGTGATGA
1801 CGGTGAAAAC CTCTGACACA TGCAGCTCCC GGAGACGGTC ACAGCTTGTC
1851 TGTAAGCGGA TGCCGGGAGC AGACAAGCCC GTCAGGGCGC GTCAGCGGGT
1901 GTTGGCGGGT GTCGGGGCGC AGCCATGACC CAGTCACGTA GCGATAGCGG
1951 AGTGTATACT GGCTTAACTA TGCGGCATCA GAGCAGATTG TACTGAGAGT
2001 GCACCATATG CGGTGTGAAA TACCGCACAG ATGCGTAAGG AGAAAATACC
2051 GCATCAGGCG CTCTTCCGCT TCCTCGCTCA CTGACTCGCT GCGCTCGGTC
2101 TGTCGGCTGC GGCGAGCGGT ATCAGCTCAC TCAAAGGCGG TAATACGGTT
2151 ATCCACAGAA TCAGGGGATA ACGCAGGAAA GAACATGTGA GCAAAAGGCC
2201 AGCAAAAGGC CAGGAACCGT AAAAAGGCCG CGTTGCTGGC GTTTTTCCAT
2251 AGGCTCCGCC CCCCTGACGA GCATCACAAA AATCGACGCT CAAGTCAGAG
2301 GTGGCGAAAC CCGACAGGAC TATAAAGATA CCAGGCGTTT CCCCCTGGAA
2351 GCTCCCTCGT GCGCTCTCCT GTTCCGACCC TGCCGCTTAC CGGATACCTG
2401 TCCGCCTTTC TCCCTTCGGG AAGCGTGGCG CTTTCTCAAT GCTCACGCTG
2451 TAGGTATCTC AGTTCGGTGT AGGTCGTTCG CTCCAAGCTG GGCTGTGTGC
2501 ACGAACCCCC CGTTCAGCCC GACCGCTGCG CCTTATCCGG TAACTATCGT
```

FIG. 2c

```
2551 CTTGAGTCCA ACCCGGTAAG ACACGACTTA TCGCCACTGG CAGCAGCCAC
2601 TGGTAACAGG ATTAGCAGAG CGAGGTATGT AGGCGGTGCT ACAGAGTTCT
2651 TGAAGTGGTG GCCTAACTAC GGCTACACTA GAAGGACAGT ATTTGGTATC
2701 TGCGCTCTGC TGAAGCCAGT TACCTTCGGA AAAAGAGTTG GTAGCTCTTG
2751 ATCCGGCAAA CAAACCACCG CTGGTAGCGG TGGTTTTTTT GTTTGCAAGC
2801 AGCAGATTAC GCGCAGAAAA AAAGGATCTC AAGAAGATCC TTTGATCTTT
2851 TCTACGGGGT CTGACGCTCA GTGGAACGAA AACTCACGTT AAGGGATTTT
2901 GGTCATGAGA TTATCAAAAA GGATCTTCAC CTAGATCCTT TTAAATTAAA
2951 AATGAAGTTT TAAATCAATC TAAAGTATAT ATGAGTAAAC TTGGTCTGAC
3001 AGTTACCAAT GCTTAATCAG TGAGGCACCT ATCTCAGCGA TCTGTCTATT
3051 TCGTTCATCC ATAGCTGCCT GACTCCCCGT CGTGTAGATA ACTACGATAC
3101 GGGAGGGCTT ACCATCTGGC CCCAGTGCTG CAATGATACC GCGAGACCCA
3151 CGCTCACCGG CTCCAGATTT ATCAGCAATA AACCAGCCAG CCGGAAGGGC
3201 CGAGCGCAGA AGTGGTCCTG CAACTTTATC CGCCTCCATC CAGTCTATTA
3251 ATTGTTGCCA GGAAGCTAGA GTAAGTAGTT CGCCAGTTAA TAGTTTGCGC
3301 AACGTTGTTG CCATTGCTAC AGGCATCGTG GTGTCACGCT CGTCGTTTGG
3351 TATGGCTTCA TTCAGCTCCG GTTCCCAACG ATCAAGGCGA GTTACATGAT
3401 CCCCCATGTT GTGCAAAAAA GCGGTTAGCT CCTTCGGTCC TCCGATCGTT
3451 GTCAGAAGTA AGTTGGCCGC AGTGTTATCA CTCATGGTTA TGGCAGCACT
3501 GCATAATTCT CTTACTGTCA TGCCATCCGT AAGATGCTTT TCTGTGACTG
3551 GTGAGTACTC AACCAAGTCA TTCTGAGAAT AGTGTATGCG GCGACCGAGT
3601 TGCTCTTGCC CGGCGTCAAT ACGGGATAAT ACCGCGCCAC ATAGCAGAAC
3651 TTTAAAAGTG CTCATCATTG GAAAACGTTC TTCGGGGCGA AAACTCTCAA
3701 GGATCTTACC GCTGTTGAGA TCCAGTTCGA TGTAACCCAC TCGTGCACCC
3751 AACTGATCTT CAGCATCTTT TACTTTCACC AGCGTTTCTG GGTGAGCAAA
3801 AACAGGAAGG CAAAATGCCG CAAAAAAGGG AATAAGGGCG ACACGGAAAT
3851 GTTGAATACT CATACTCTTC CTTTTTCAAT ATTATTGAAG CATTTATCAG
3901 GGTTATTGTC TCATGAGCGG ATACATATTT GAATGTATTT AGAAAAATAA
```

FIG. 2d

3951 ACAAATAGGG GTTCCGCGCA CATTTCCCCG AAAAGTGCCA CCTGACGTCT

4001 AAGAAACCAT TATTATCATG ACATTAACCT ATAAAAATAG GCGTATCACG

4051 AGGCCCTTTC GTCTTCAC

FIG. 4a

```
              10         20         30         40         50
               |          |          |          |          |
   1 AAGCTTCAGG CTGCCGCAAG CACTCAGGGC GCAAGGGCTG CTAAAGGAAG
  51 CGGAACACGT AGAAAGCCAG TCCGCAGAAA CGGTGCTGAC CCCGGATGAA
 101 TGTCAGCTAC TGGGCTATCT GGACAAGGGA AAACGCAAGC GCAAAGAGAA
 151 AGCAGGTAGC TTGCAGTGGG CTTACATGGC GATAGCTAGA CTGGGCGGTT
 201 TTATGGACAG CAAGCGAACC GGAATTGCCA GCTGGGGCGC CCTCTGGTAA
 251 GGTTGGGAAG CCCTGCAAAG TAAACTGGAT GGCTTTCTTG CCGCCAAGGA
 301 TCTGATGGCG CAGGGGATCA AGATCTGATC AAGAGACAGG ATGAGGATCG
 351 TTTCGCATGA TTGAACAAGA TGGATTGCAC GCAGGTTCTC CGGCCGCTTG
 401 GGTGGAGAGG CTATTCGGCT ATGACTGGGC ACAACAGACA ATCGGCTGCT
 451 CTGATGCCGC CGTGTTCCGG CTGTCAGCGC AGGGGCGCCC GGTTCTTTTT
 501 GTCAAGACCG ACCTGTCCGG TGCCCTGAAT GAACTGCAGG ACGAGGCAGC
 551 GCGGCTATCG TGGCTGGCCA CGACGGGCGT TCCTTGCGCA GCTGTGCTCG
 601 ACGTTGTCAC TGAAGCGGGA AGGGACTGGC TGCTATTGGG CGAAGTGCCG
 651 GGGCAGGATC TCCTGTCATC TCACCTTGCT CCTGCCGAGA AAGTATCCAT
 701 CATGGCTGAT GCAATGCGGC GGCTGCATAC GCTTGATCCG GCTACCTGCC
 751 CATTCGACCA CCAAGCGAAA CATCGCATCG AGCGAGCACG TACTCGGATG
 801 GAAGCCGGTC TTGTCGATCA GGATGATCTG GACGAAGAGC ATCAGGGGCT
 851 CGCGCCAGCC GAACTGTTCG CCAGGCTCAA GGCGCGCATG CCCGACGGCG
 901 AGGATCTCGT CGTGACCCAT GGCGATGCCT GCTTGCCGAA TATCATGGTG
 951 GAAAATGGCC GCTTTTCTGG ATTCATCGAC TGTGGCCGGC TGGGTGTGGC
1001 GGACCGCTAT CAGGACATAG CGTTGGCTAC CCGTGATATT GCTGAAGAGC
1051 TTGGCGGCGA ATGGGCTGAC CGCTTCCTCG TGCTTTACGG TATCGCCGCT
1101 CCCGATTCGC AGCGCATCGC CTTCTATCGC CTTCTTGACG AGTTCTTCTG
1151 AGCGGGACTC TGGGGTTCGA AATGACCGAC CAAGCGACGC CCAACCTGCC
```

FIG. 4b

```
1201 ATCACGAGAT TTCGATTCCA CCGCCGCCTT CTATGAAAGG TTGGGCTTCG
1251 GAATCGTTTT CCGGGACGCC GGCTGGATGA TCCTCCAGCG CGGGGATCTC
1301 ATGCTGGAGT TCTTCGCCCA CCCCGGGCTC GATCCCCTCG CGAGTTGGTT
1351 CAGCTGCTGC CTGAGGCTGG ACGACCTCGC GGAGTTCTAC CGGCAGTGCA
1401 AATCCGTCGG CATCCAGGAA ACCAGCAGCG GCTATCCGCG CATCCATGCC
1451 CCCGAACTGC AGGAGTGGGG AGGCACGATG GCCGCTTTGG TCGACAATTC
1501 GCGCTAACTT ACATTAATTG CGTTGCGCTC ACTGCCCGCT TTCCAGTCGG
1551 GAAACCTGTC GTGCCAGCTG CATTAATGAA TCGGCCAACG CGCGGGGAGA
1601 GGCGGTTTGC GTATTGGGCG CCAGGGTGGT TTTTCTTTTC ACCAGTGAGA
1651 CGGGCAACAG CTGATTGCCC TTCACCGCCT GGCCCTGAGA GAGTTGCAGC
1701 AAGCGGTCCA CGCTGGTTTG CCCCAGCAGG CGAAAATCCT GTTTGATGGT
1751 GGTTAACGGC GGGATATAAC ATGAGCTGTC TTCGGTATCG TCGTATCCCA
1801 CTACCGAGAT ATCCGCACCA ACGCGCAGCC CGGACTCGGT AATGGCGCGC
1851 ATTGCGCCCA GCGCCATCTG ATCGTTGGCA ACCAGCATCG CAGTGGGAAC
1901 GATGCCCTCA TTCAGCATTT GCATGGTTTG TTGAAAACCG GACATGGCAC
1951 TCCAGTCGCC TTCCCGTTCC GCTATCGGCT GAATTTGATT GCGAGTGAGA
2001 TATTTATGCC AGCCAGCCAG ACGCAGACGC GCCGAGACAG AACTTAATGG
2051 GCCCGCTAAC AGCGCGATTT GCTGGTGACC CAATGCGACC AGATGCTCCA
2101 CGCCCAGTCG CGTACCGTCT TCATGGGAGA AAATAATACT GTTGATGGGT
2151 GTCTGGTCAG AGACATCAAG AAATAACGCC GGAACATTAG TGCAGGCAGC
2201 TTCCACAGCA ATGGCATCCT GGTCATCCAG CGGATAGTTA ATGATCAGCC
2251 CACTGACGCG TTGCGCGAGA AGATTGTGCA CCGCCGCTTT ACAGGCTTCG
2301 ACGCCGCTTC GTTCTACCAT CGACACCACC ACGCTGGCAC CCAGTTGATC
2351 GGCGCGAGAT TAATCGCCG CGACAATTTG CGACGGCGCG TGCAGGGCCA
2401 GACTGGAGGT GGCAACGCCA ATCAGCAACG ACTGTTTGCC CGCCAGTTGT
2451 TGTGCCACGC GGTTGGGAAT GTAATTCAGC TCCGCCATCG CCGCTTCCAC
2501 TTTTTCCCGC GTTTTCGCAG AAACGTGGCT GGCCTGGTTC ACCACGCGGG
```

FIG. 4c

2551 <u>AAACGGTCTG ATAAGAGACA CCGGCATACT CTGCGACATC GTATAACGTT</u>

2601 <u>ACTGGTTTCA</u> CATTCACCAC CCTGAATTGA CTCTCTTCCG GGCGCTATCA

2651 TGCCATACCG CGAAAGGTTT TGCACCATTC GATGGTGTCA ACGTAAATGC

2701 ATGCCGCTTC GCCTTCGCGC GCGAA<u>TTGTC GAC</u>CCTGTCC CTCCTGTTCA

2751 GCTACTGACG GGTGGTGCG TAACGGCAAA AGCACCGCCG GACATCAGCG

2801 CTAGCGGAGT GTATACTGGC TTACTATGTT GGCACTGATG AGGGTGTCAG

2851 TGAAGTGCTT CATGTGGCAG GAGAAAAAAG CTGCACCGG TGCGTCAGCA

2901 GAATATGTGA TACAGGATAT ATTCCGCTTC CTCGCTCACT GACTCGCTAC

2951 GCTCGGTCGT TCGACTGCGG CGAGCGGAAA TGGCTTACGA ACGGGGCGGA

3001 GATTTCCTGG AAGATGCCAG GAAGATACTT AACAGGGAAG TGAGAGGGCC

3051 GCGGCAAAGC CGTTTTTCCA TAGGCTCCGC CCCCCTGACA AGCATCACGA

3101 AATCTGACGC TCAAATCAGT GGTGGCGAAA CCCGACAGGA CTATAAAGAT

3151 ACCAGGCGTT TCCCCTGGCG GCTCCCTCGT GCGCTCTCCT GTTCCTGCCT

3201 TTCGGTTTAC CGGTGTCATT CCGCTGTTAT GGCCGCGTTT GTCTCATTCC

3251 ACGCCTGACA CTCAGTTCCG GGTAGGCAGT TCGCTCCAAG CTGGACTGTA

3301 TGCACGAACC CCCCGTTCAG TCCGACCGCT GCGCCTTATC CGGTAACTAT

3351 CGTCTTGAGT CCAACCCGGA AAGACATGCA AAAGCACCAC TGGCAGCAGC

3401 CACTGGTAAT TGATTTAGAG GAGTTAGTCT TGAAGTCATG CGCCGGTTAA

3451 GGCTAAACTG AAAGGACAAG TTTTGGTGAC TGCGCTCCTC CAAGCCAGTT

3501 ACCTCGGTTC AAAGAGTTGG TAGCTCAGAG AACCTTCGAA AAACCGCCCT

3551 GCAAGGCGGT TTTTTCGTTT TCAGAGCAAG AGATTACGCG CAGACCAAAA

3601 CGATCTCAAG AAGATCATCT TATTAATCAG ATAAAATATT TCTAGATTTC

3651 AGTGCAATTT ATCTCTTCAA ATGTAGCACC TGAAGTCAGC CCCATACGAT

3701 ATAAGTTGTT AATTCTCATG TTTGACAGCT TATCATCGAT

FIG. 8

|   | —MW-ST. | —RO-33 | —RO-56 | —Gen.-13 | —H-B3 | —RO-53 | —R-FCR-3 | —MAD-20 | —542 | —RO-58 | —FCH-5C2 | —K1 |
|---|---|---|---|---|---|---|---|---|---|---|---|---|
| 97— | | | | | | | | | | | | |
| 67— | | | | | | | | | | | | |
| 43— | | — | — | | — | | | | | | | |
| 26— | | | | | | | | | | | | |

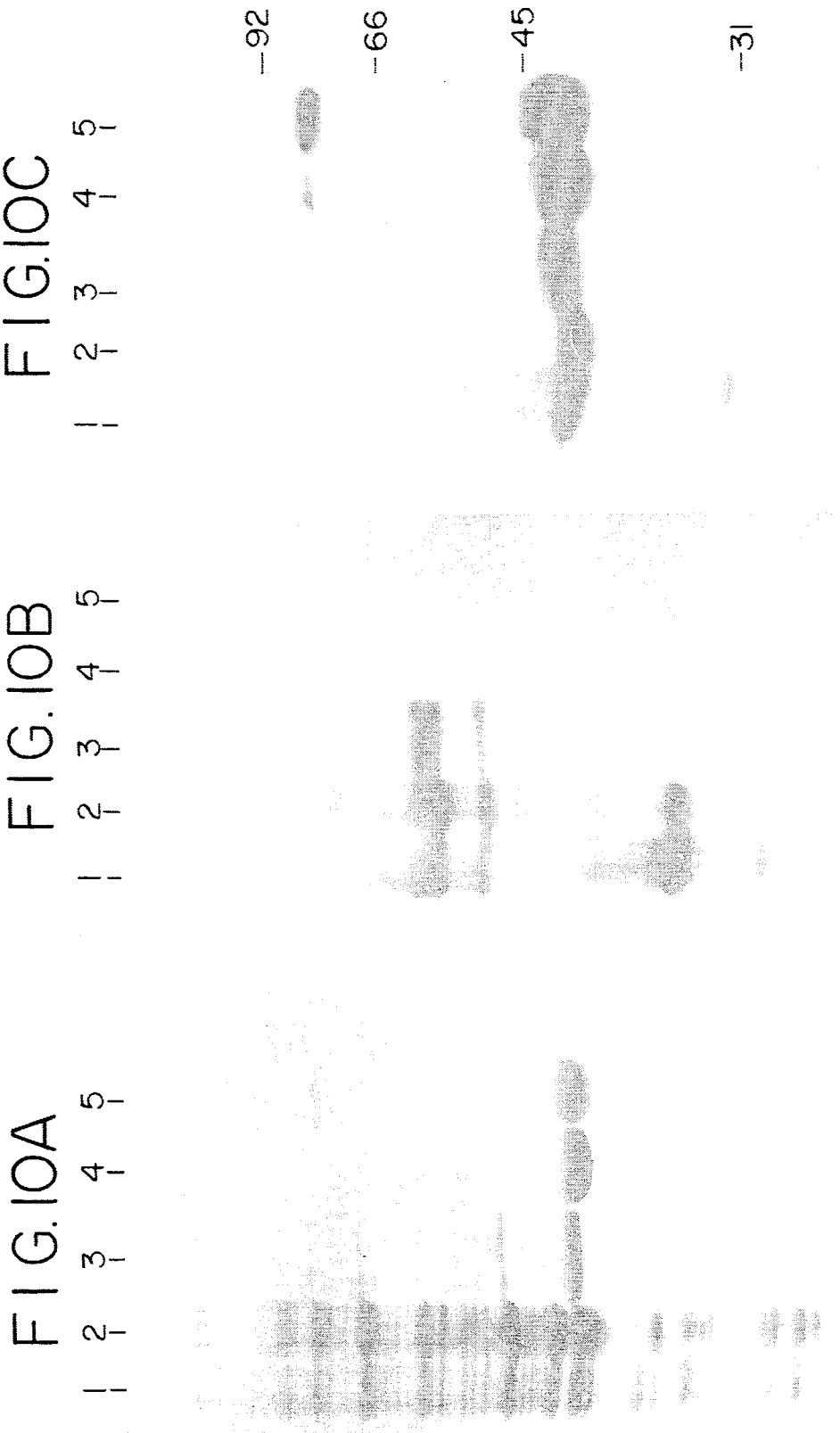

FIG. IIa

```
         10         20         30         40         50         60
         |          |          |          |          |          |
CTCGAGAAAT CATAAAAAAT TTATTTGCTT TGTGAGCGGA TAACAATTAT AATAGATTCA
GAGCTCTTTA GTATTTTTTA AATAAACGAA ACACTCGCCT ATTGTTAATA TTATCTAAGT

ATTGTGAGCG GATAACAATT TCACACAGAA TTCATTAAAG AGGAGAAATT AACTATGAGA
TAACACTCGC CTATTGTTAA AGTGTGTCTT AAGTAATTTC TCCTCTTTAA TTGATACTCT

GGATCGCATC ACCATCACCA TCACGGATCC GAGCTTGCAT GCCAATATAT GAATGCCCCA
CCTAGCGTAG TGGTAGTGGT AGTGCCTAGG CTCGAACGTA CGGTTATATA CTTACGGGGT

AAAAAATTAC CAGCAGATGT TGCCGAAGAA TTAGCAACCA CCGCCCAAAA GCTTGTTCAA
TTTTTTAATG GCTGTCTACA ACGGCTTCTT AATCGTTGGT GGCGGGTTTT CGAACAAGTT

GCTGGAAAGG GAATTTTAGC TGCTGATGAA TCAACACAAA CCATTAAGAA AAGATTCGAC
CGACCTTTCC CTTAAAATCG ACGACTACTT AGTTGTGTTT GGTAATTCTT TTCTAAGCTG

AACATCAAAT TAGAGAACAC AATAGAAAAC AGAGCTAGCT ACAGAGATTT ATTATTTGGA
TTGTAGTTTA ATCTCTTGTG TTATCTTTTG TCTCGATCGA TGTCTCTAAA TAATAAACCT

ACTAAAGGAT TAGGAAAATT CATTTCAGGA GCAATTTTAT TTGAAGAAAC ATTATTTCAA
TGATTTCCTA ATCCTTTTAA GTAAAGTCCT CGTTAAAATA AACTTCTTTG TAATAAAGTT

AAGAATGAAG CCGGTGTACC ACAGGTTAAT TTATTACACA ATGAAAATAT AATTCCAGGT
TTCTTACTTC GGCCACATGG TGTCCAATTA AATAATGTGT TACTTTTATA TTAAGGTCCA

ATTAAGGTTG ATAAAGGTTT GGTTAACATT CCATGCACAG ATGAAGAAAA ATCAACTCAA
TAATTCCAAC TATTTCCAAA CCAATTGTAA GGTACGTGTC TACTTCTTTT TAGTTGAGTT

TGTTTAGATG GATTAGCAGA AAGATGCAAA GAGTATTATA AAGCTGGTGC AAGGTTTGCT
ACAAATCTAC CTAATCGTCT TTCTACGTTT CTCATAATAT TTCGACCACG TTCCAAACGA

AAATGGAGAA CAGTTTTAGT TATTGACACA GCCAAAGGAA AACCAACTGA TTTATCAAAT
TTTACCTCTT GTCAAAATCA ATAACTGTGT CGGTTTCCTT TTGGTTGACT AAATAGTTTA

CACGAAACTG CATGGGGATT GGCTAGATAT GCATCTATTT GTCAACAAAA TAGATTAGTT
GTGCTTTGAC GTACCCCTAA CCGATCTATA CGTAGATAAA CAGTTGTTTT ATCTAATCAA

CACGAAACTG CATGGGGATT GGCTAGATAT GCATCTATTT GTCAACAAAA TAGATTAGTT
GTGCTTTGAC GTACCCCTAA CCGATCTATA CGTAGATAAA CAGTTGTTTT ATCTAATCAA

CCAATTGTTG AACCTGAAAT TTAGCTGAT GGACCACACT CAATTGAAGT TTGCGCAGTT
GGTTAACAAC TTGGACTTTA AAATCGACTA CCTGGTGTGA GTTAACTTCA AACGCGTCAA

GTAAACTCAAA AAGTTTTATC ATGTGTATTT AAAGCTTTAC AAGAAAATGG TGTATTATTA
CATTGAGTTT TTCAAAATAG TACACATAAA TTTCGAAATG TTCTTTTACC ACATAATAAT

GAAGGTGCAT TGTTAAAACC AAACATGGTT ACTGCTGGTT ATGAATGTAC TGCTAAAACC
CTTCCACGTA ACAATTTTGG TTTGTACCAA TGACGACCAA TACTTACATG ACGATTTTGG

ACTACTCAAG ATGTTGGTTT CTTAACTGTC AGAACCTTAA GGAGAACTGT ACCACCAGCC
TGATGAGTTC TACAACCAAA GAATTGACAG TCTTGGAATT CCTCTTGACA TGGTGGTCGG
```

FIG. IIb

```
TTACCAGGTG TTGTATTTTT ATCTGGAGGA CAATCAGAAG AAGAGGCTTC TGTTAATTTA
AATGGTCCAC AACATAAAAA TAGACCTCCT GTTAGTCTTC TTCTCCGAAG ACAATTAAAT

AATTCAATCA ATGCTTTGGG TCCACACCCA TGGGCTTTAA CCTTCTCTTA CGGTAGAGCT
TTAAGTTAGT TACGAAACCC AGGTGTGGGT ACCCGAAATT GGAAGAGAAT GCCATCTCGA

TTACAAGCTT CAGTATTGAA CACATGGCAA GGAAAGAAAG AAAATGTTGC AAAGGCAAGA
AATGTTCGAA GTCATAACTT GTGTACCGTT CCTTTCTTTC TTTTACAACG TTTCCGTTCT

GAAGTTTTAT TACAAAGAGC TGAAGCCAAC TCCTTAGCAA CTTATGGTAA ATACAAAGGA
CTTCAAAATA ATGTTTCTCG ACTTCGGTTG AGGAATCGTT GAATACCATT TATGTTTCCT
                                                              (T)
GGTGCAGGTG GTGAAAATGC AGGTGCTTCA TTATATGAAA AGAAATATGT CTATTAAAAA
CCACGTCCAC CACTTTTACG TCCACGAAGT AATATACTTT TCTTTATACA GATAATTTTT

CTTCACCAAC CAAAAATGAA TAATAATAAT AATAAATAAA TTACTAAATG AATGGTACTA
GAAGTGGTTG GTTTTTACTT ATTATTATTA TTATTTATTT AATGATTTAC TTACCATGAT

TATTTTTAAA AATAAGGGTA ATATATTTTC TGTATGTATA TATATATATA TATATACAAA
ATAAAAATTT TTATTCCCAT TATATAAAAG ACATACATAT ATATATATAT ATATATGTTT

ATATGTGAAA TTATAAAAAA AAAAAAAAAA AAAAAAAGGA ATTCCGGATC CTCCGGCATC
TATACACTTT AATATTTTTT TTTTTTTTTT TTTTTTTCCT TAAGGCCTAG GAGGCCGTAG

ATGGTTCGAC CATTGAACTG CATCGTCGCC GTGTCCCAAA ATATGGGGAT TGGCAAGAAC
TACCAAGCTG GTAACTTGAC GTAGCAGCGG CACAGGGTTT TATACCCCTA ACCGTTCTTG

GGAGACCTAC CCTGGCCTCC GCTCAGGAAC GAGTTCAAGT ACTTCCAAAG AATGACCACA
CCTCTGGATG GGACCGGAGG CGAGTCCTTG CTCAAGTTCA TGAAGGTTTC TTACTGGTGT

ACCTCTTCAG TGGAAGGTAA ACAGAATCTG GTGATTATGG GTAGGAAAAC CTGGTTCTCC
TGGAGAAGTC ACCTTCCATT TGTCTTAGAC CACTAATACC CATCCTTTTG GACCAAGAGG

ATTCCTGAGA AGAATCGACC TTTAAAGGAC AGAATTAATA TAGTTCTCAG TAGAGAACTC
TAAGGACTCT TCTTAGCTGG AAATTTCCTG TCTTAATTAT ATCAAGAGTC ATCTCTTGAG

AAAGAACCAC CACGAGGAGC TCATTTTCTT GCCAAAAGTT TGGATGATGC CTTAAGACTT
TTTCTTGGTG GTGCTCCTCG AGTAAAAGAA CGGTTTTCAA ACCTACTACG GAATTCTGAA

ATTGAACAAC CGGAATTGGC AAGTAAAGTA GACATGGTTT GGATAGTCGG AGGCAGTTCT
TAACTTGTTG GCCTTAACCG TTCATTTCAT CTGTACCAAA CCTATCAGCC TCCGTCAAGA

GTTTACCAGG AAGCCATGAA TCAACCAGGC CACCTTAGAC TCTTTGTGAC AAGGATCATG
CAAATGGTCC TTCGGTACTT AGTTGGTCCG GTGGAATCTG AGAAACACTG TTCCTAGTAC

CAGGAATTTG AAAGTGACAC GTTTTTCCCA GAAATTGATT TGGGGAAATA TAAACTTCTC
GTCCTTAAAC TTTCACTGTG CAAAAAGGGT CTTTAACTAA ACCCCTTTAT ATTTGAAGAG

CCAGAATACC CAGGCGTCCT CTCTGAGGTC CAGGAGGAAA AAGGCATCAA GTATAAGTTT
GGTCTTATGG GTCCGCAGGA GAGACTCCAG GTCCTCCTTT TTCCGTAGTT CATATTCAAA

GAAGTCTACG AGAAGAAAGG TTCCAGATCT GTTAACCTAG TTTAACAGGA AGATGCTTTC
CTTCAGATGC TCTTCTTTCC AAGGTCTAGA CAATTGGATC AAATTGTCCT TCTACGAAAG
```

FIG. IIc

```
AAGTTCTCTG CTCCCCTCCT AAAGCTATGC ATTTTTATAA GACCATGGGA CTTTTGCTGG
TTCAAGAGAC GAGGGGAGGA TTTCGATACG TAAAAATATT CTGGTACCCT GAAAACGACC

CTTTAGATCC GGCCAAGCTT GGACTCCTGT TGATAGATCC AGTAATGACC TCAGAACTCC
GAAATCTAGG CCGGTTCGAA CCTGAGGACA ACTATCTAGG TCATTACTGG AGTCTTGAGG

ATCTGGATTT GTTCAGAACG CTCGGTTGCC GCCGGGCGTT TTTTATTGGT GAGAATCCAA
TAGACCTAAA CAAGTCTTGC GAGCCAACGG CGGCCCGCAA AAAATAACCA CTCTTAGGTT

GCTAGCTTGG CGAGATTTTC TCCTCGATTC CTTCGATTTT ACCTCTTTTT TTAGTGACCT
CGATCGAACC GCTCTAAAAG TCCTCGATTC CTTCGATTTT ACCTCTTTTT TTAGTGACCT

TATACCACCG TTGATATATC CCAATGGCAT CGTAAAGAAC ATTTTGAGGC ATTTCAGTCA
ATATGGTGGC AACTATATAG GGTTACCGTA GCATTTCTTG TAAAACTCCG TAAAGTCAGT

GTTGCTCAAT GTACCTATAA CCAGACCGTT CAGCTGGATA TTACGGCCTT TTTAAAGACC
CAACGAGTTA CATGGATATT GGTCTGGCAA GTCGACCTAT AATGCCGGAA AAATTTCTGG

GTAAAGAAAA ATAAGCACAA GTTTTATCCG GCCTTTATTC ACATTCTTGC CCGCCTGATG
CATTTCTTTT TATTCGTGTT CAAAATAGGC CGGAAATAAG TGTAAGAACG GGCGGACTAC

AATGCTCATC CGGAATTTCG TATGGCAATG AAAGACGGTG AGCTGGTGAT ATGGGATAGT
TTACGAGTAG GAATTAAAGC ATACCGTTAC TTTCTGCCAC TCGACCACTA TACCCTATCA

GTTCACCCTT GTTACACCGT TTTCCATGAG CAAACTGAAA CGTTTTCATC GCTCTGGAGT
CAAGTGGGAA CAATGTGGCA AAAGGTACTC GTTTGACTTT GCAAAAGTAG CGAGACCTCA

GAATACCACG ACGATTTCCG GCAGTTTCTA CACATATATT CGCAAGATGT GGCGTGTTAC
CTTATGGTGC TGCTAAAGGC CGTCAAAGAT GTGTATATAA GCGTTCTACA CCGCACAATG

GGTGAAAACC TGGCCTATTT CCCTAAAGGG TTTATTGAGA ATATGTTTTT CGTCTCAGCC
CCACTTTTGG ACCGGATAAA GGGATTTCCC AAATAACTCT TATACAAAAA GCAGAGTCGG

AATCCCTGGG TGAGTTTCAC CAGTTTTGAT TTAAACGTGG CCAATATGGA CAACTTCTTC
TTAGGGACCC ACTCAAAGTG GTCAAAACTA AATTTGCACC GGTTATACCT GTTGAAGAAG

GCCCCCGTTT TCACCATGGG CAAATATTAT ACGCAAGGCG ACAAGGTGCT GATGCCGCTG
CAAAAACAAA AGTGGTACCC GTTTATAATA TGCGTTCCGC TGTTCCACGA CTACGGCGAC

GCGATTCAGG TTCATCATGC CGTCTGTGAT GGCTTCCATG TCGGCAGAAT GCTTAATGAA
CGCTAAGTCC AAGTAGTACG GCAGACACTA CCGAAGGTAC AGCCGTCTTA CGAATTACTT

TTACAACAGT ACTGCGATGA GTGGCAGGGC GGGGCGTAAT TTTTTTAAGG CAGTTATTGG
AATGTTGTCA TGACGCTACT CACCGTCCCG CCCCGCATTA AAAAAATTCC GTCAATAACC

TGCCCTTAAA CGCCTGGGGT AATGACTCTC TAGCTTGAGG CATCAAATAA AACGAAAGGC
ACGGGAATTT GCGGACCCCA TTACTGAGAG ATCGAACTCC GTAGTTTATT TTGCTTTCCG

TCAGTCGAAA GACTGGGCCT TTCGTTTTAT CTGTTGTTTG TCGGTGAACG CTCTCCTGAG
AGTCAGCTTT CTGACCCGGA AAGCAAAATA GACAACAAAC AGCCACTTGC GAGAGGACTC

TAGGACAAAT CCGCCGCTCT AGAGCTGCCT CGCGCGTTTC GGTGATGACG GTGAAAACCT
ATCCTGTTTA GGCGGCGAGA TCTCGACGGA GCGCGCAAAG CCACTACTGC CACTTTTGGA

CTGACACATG CAGCTCCCGG AGACGGTCAC AGCTTGTCTG TAAGCGGATG CCGGGAGCAG
```

FIG. IId

```
GACTGTGTAC GTCGAGGGCC TCTGCCAGTG TCGAACAGAC ATTCGCCTAC GGCCCTCGTC

ACAAGCCCGT CAGGGCGCGT CAGCGGGTGT TGGCGGGTGT CGGGGCGCAG CCATGACCCA
TGTTCGGGCA GTCCCGCGCA GTCGCCCACA ACCGCCCACA GCCCCGCGTC GGTACTGGGT

GTCACGTAGC GATAGCGGAG TGTATACTGG CTTAACTATG CGGCATCAGA GCAGATTGTA
CAGTGCATCG CTATCGCCTC ACATATGACC GAATTGATAC GCCGTAGTCT CGTCTAACAT

CTGAGAGTGC ACCATATGCG GTGTGAAATA CCGCACAGAT GCGTAAGGAG AAAATACCGC
GACTCTCACG TGGTATACGC CACACTTTAT GGCGTGTCTA CGCATTCCTC TTTTATGGCG

ATCAGGCGCT CTTCCGCTTC CTCGCTCACT GACTCGCTGC GCTCGGTCTG TCGGCTGCGG
TAGTCCGCGA GAAGGCGAAG GAGCGSGTGA CTGAGCGACG CGAGCCAGAC AGCCGACGCC

CGAGCGGTAT CAGCTCACTC AAAGGCGGTA ATACGGTTAT CCACAGAATC AGGGGATAAC
GCTCGCCATA GTCGAGTGAG TTTCCGCCAT TATGCCAATA GGTGTCTTAG TCCCCTATTG

GCAGGAAAGA ACATGTGAGC AAAAGGCCAG CAAAAGGCCA GGAACCGTAA AAAGGCCGCG
CGTCCTTTCT TGTACACTCG TTTTCCGGTC GTTTTCCGGT CCTTGGCATT TTTCCGGCGC

TTGCTGGCGT TTTTCCATAG GCTCCGCCCC CCTGACGAGC ATCACAAAAA TCGACGCTCA
AACGACCGCA AAAAGGTATC CGAGGCGGGG GGACTGCTCG TAGTGTTTTT AGCTGCGAGT

AGTCAGAGGT GGCGAAACCC GACAGGACTA TAAAGATACC AGGCGTTTCC CCCTGGAAGC
TCAGTCTCCA CCGCTTTGGG CTGTCCTGAT ATTTCTATGG TCCGCAAAGG GGGACCTTCG

TCCCTCGTGC GCTCTCCTGT TCCGACCCTG CCGCTTCCCG GATACCTGTC CGCCTTTCTC
AGGGAGCACG CGAGAGGACA AGGCTGGGAC GGCGAATGGC CTATGGACAG GCGGAAAGAG

CCTTCGGGAA GCGTGGCGCT TTCTCAATGC TCACGCTGTC GGTATCTCAG TTCGGTGTAG
GGAAGCCCTT CGCACCGCGA AAGAGTTACG AGTGCGACAT CCATAGAGTC AAGCCACATC

GTCGTTCGCT CCAAGCTGGG CTGTGTGCAC GAACCCCCCG TTCAGCCCGA CCGCTGCGCC
CAGCAAGCGA GGTTCGACCC GACACACGTG CTTGGGGGGC AAGTCGGGCT GGCGACGCGG

TTATCCGGTA ACTATCGTCT TGAGTCCAAC CCGGTAAGAC ACGACTTATC GCCACTGGCA
AATAGGCCAT TGATAGCAGA ACTCAGGTTG GGCCATTCTG TGCTGAATAG CGGTGACCGT

GCAGCCACTG GTAACAGGAT TAGCAGAGCG AGGTATGTAG GCGGTGCTAC AGAGTTCTTG
CGTCGGTGAC CATTGTCCTA ATCGTCTCGC TCCATACATC CGCCACGATG TCTCAAGAAC

AAGTGGTGGC CTAACTACGG CTACACTAGA AGGACAGTAT TTGGTATCTG CGCTCTGCTG
TTCACCACCG GATTGATGCC GATGTGATCT TCCTGTCATA AACCATAGAC GCGAGACGAC

AAGCCAGTTA CCTTCGGAAA AAGAGTTGGT AGCTCTTGAT CCGGCAAACA AACCACCGCT
TTCGGTCAAT GGAAGCCTTT TTCTCAACCA TCGAGAACTA GGCCGTTTGT TTGGTGGCGA

GGTAGCGGTG GTTTTTTTGT TTGCAAGCAG CAGATTACGC GCAGAAAAAA AGGATCTCAA
CCATCGCCAC CAAAAAAACA AACGTTCGTC GTCTAATGCG CGTCTTTTTT TCCTAGAGTT

GAAGATCCTT TGATCTTTTC TACGGGGTCT GACGCTCAGT GGAACGAAAA CTCACGTTAA
CTTCTAGGAA ACTAGAAAAG ATGCCCCAGA CTGCGAGTCA CCTTGCTTTT GAGTGCAATT

GGGATTTTGG TCATGAGATT ATCAAAAAGG ATCTTCACCT AGATCCTTTT AAATTAAAAA
CCCTAAAACC AGTACTCTAA TAGTTTTTCC TAGAAGTGGA TCTAGGAAAA TTTAATTTTT
```

FIG. IIe

```
TGAAGTTTTA AATCAATCTA AAGTATATAT GAGTAAACTT GGTCTGACAG TTACCAATGC
ACTTCAAAAT TTAGTTAGAT TTCATATATA CTCATTTGAA CCAGACTGTC AATGGTTACG

TTAATCAGTG AGGCACCTAT CTCAGCGATC TGTCTATTTC GTTCATCCAT AGCTGCCTGA
AATTAGTCAC TCCGTGGATA GAGTCGCTAG ACAGATAAAG CAAGTAGGTA TCGACGGACT

CTCCCCGTCG TGTAGATAAC TACGATACGG GAGGGCTTAC CATCTGGCCC CAGTGCTGCA
GAGGGGCAGC ACATCTATTG ATGCTATGCC CTCCCGAATG GTAGACCGGG GTCACGACGT

ATGATACCGC GAGACCCACG CTCACCGGCT CCAGATTTAT CAGCAATAAA CCAGCCAGCC
TACTATGGCG CTCTGGGTGC GAGTGGCCGA GGTCTAAATA GTCGTTATTT GGTCGGTCGG

GGAAGGGCCG AGCGCAGAAG TGGTCCTGCA ACTTTATCCG CCTCCATCCA GTCTATTAAT
CCTTCCCGGC TCGCGTCTTC ACCAGGACGT TGAAATAGGC GGAGGTAGGT CAGATAATTA

TGTTGCCGGG AAGCTAGAGT AAGTAGTTCG CCAGTTAATA GTTTGCGCAA CGTTGTTGCC
ACAACGGCCC TTCGATCTCA TTCATCAAGC GGTCAATTAT CAAACGCGTT GCAACAACGG

ATTGCTACAG GCATCGTGGT GTCACGCTCG TCGTTTGGTA TGGCTTCATT CAGCTCCGGT
TAACGATGTC CGTAGCACCA CAGTGCGAGC AGCAAACCAT ACCGAAGTAA GTCGAGGCCA

TCCCAACGAT CAAGGCGAGT TACATGATCC CCCATGTTGT GCAAAAAAGC GGTTAGCTCC
AGGGTTGCTA GTTCCGCTCA ATGTACTAGG GGGTACAACA CGTTTTTTCG CCAATCGAGG

TTCGGTCCTC CGATCGTTGT CAGAAGTAAG TTGGCCGCAG TGTTATCACT CATGGTTATG
AAGCCAGGAG GCTAGCAACA GTCTTCATTC AACCGGCGTC ACAATAGTGA GTACCAATAC

GCAGCACTGC ATAATTCTCT TACTGTCATG CCATCCGTAA GATGCTTTTC TGTGAACTGGT
CGTCGTGACG TATTAAGAGA ATGACAGTAC GGTAGGCATT CTACGAAAAG ACACTGACCA

GAGTACTCAA CCAAGTCATT CTGAGAATAG TGTATGCGGC GACCGAGTTG CTCTTGCCCG
CTCATGAGTT GGTTCAGTAA GACTCTTATC ACATACGCCG CTGGCTCAAC GAGAACGGGC

GCGTCAATAC GGGATAATAC CGCGCCACAT AGCAGAACTT TAAAAGGTGCT CATCATTGGA
CGCAGTTATG CCCTATTATG GCGCGGTGTA TCGTCTTGAA ATTTTCACGA GTAGTAACCT

AAACGTTCTT CGGGGCGAAA ACTCTCAAGG ATCTTACCGC TGTTGAGATC CAGTTCGATG
TTTGCAAGAA GCCCCGCTTT TGAGAGTTCC TAGAATGGCG ACAACTCTAG GTCAAGCTAC

TAACCCACTC GTGCACCCAA CTGATCTTCA GCATCTTTTA CTTTCACCAG CGTTTCTGGG
ATTGGGTGAG CACGTGGGTT GACTAGAAGT CGTAGAAAAT GAAAGTGGTC GCAAAGACCC

TGAGCAAAAA CAGGAAGGCA AAATGCCGCA AAAAAGGGAA TAAGGGCGAC ACGGAAATGT
ACTCGTTTTT GTCCTTCCGT TTTACGGCGT TTTTTCCCTT ATTCCCGCTG TGCCTTTACA

TGAATACTCA TACTCTTCCT TTTTCAATAT TATTGAAGCA TTTATCAGGG TTATTGTCTC
ACTTATGAGT ATGAGAAGGA AAAAGTTATA ATAACTTCGT AAATAGTCCC AATAACAGAG

ATGAGAGGAT ACATATTTGA ATGTATTTAG AAAAATAAAC AAATAGGGGT TCCGCGCACA
TACTCGCCTA TGTATAAACT TACATAAATC TTTTTATTTG TTTATCCCCA AGGCGCGTGT

TTTCCCCGAA AAGTGCCACC TGACGTCTAA GAAACCATTA TTATCATGAC ATTAACCTAT
AAAGGGGCTT TTCACGGTGG ACTGCAGATT CTTTGGTAAT AATAGTACTG TAATTGGATA

AAAATAGGC GTATCACGAG GCCCTTTCGT CTTCAC
TTTTTATCCG CATAGTGCTC CGGGAAAGCA GAAGTG
```

FIG. 12a

ATATATATTTATATACTATTATATATGTATTCATTTTATTCTGCTCACATTATTTATGCAT

ATGCTTCCTTTATAATAAATATATTCGTATTAACATTCAAGAAATGAGGAACGAAATATT

CCTTAATTTACATATGTATTTTTTTATTAATTGAAAAAAAAAAAAAAAATAGTAAAAATA

AGTATAGGCATATATTGAATAATGTGCTGTTGAATTGATTTATATATATATATATATATA

TATATGTATATTTATTTATATTTATACATATGGGAATATTATATATTTTCCTTTTTTCTT

⌐→M25
ATTTTTATATTTTTATATTTTTTTAGGCTCATTGCACTGAATAT
       ●
       10         20         30         40

ATG AAT GCC CCA AAA AAA TTA CCA GCA GAT GTT GCC GAA GAA TTA

MEY Asn Ala Pro Lys Lys Leu Pro Ala Asp Val Ala Glu Glu Leu 50        60        70        80        90

GCA ACC ACC GCC CAA AAG CTT GTT CAA GCT GGA AAG GGA ATT TTA

Ala Thr Thr Ala Gln Lys Leu Val Gln Ala Gly Lys Gly Ile Leu 100      110      120      130

GCT GCT GAT GAA TCA ACA CAA ACC ATT AAG AAA AGA TTC GAC AAC

Ala Ala Asp Glu Ser Thr Gln Thr Ile Lys Lys Arg Phe Asp Asn 140      150      160      170      180

ATC AAA TTA GAG AAC ACA ATA GAA AAC AGA GCT AGC TAC AGA GAT

Ile Lys Leu Glu Asn Thr Ile Glu Asn Arg Ala Ser Tyr Arg Asp 190      200      210      220

TTA TTA TTT GGA ACT AAA GGA TTA GGA AAA TTC ATT TCA GGA GCA

Leu Leu Phe Gly Thr Lys Gly Leu Gly Lys Phe Ile Ser Gly Ala 230      240      250      260      270

ATT TTA TTT GAA GAA ACA TTA TTT CAA AAG AAT GAA GCC GGT GTA

Ile Leu Phe Glu Glu Thr Leu Phe Gln Lys Asn Glu Ala Gly Val

FIG. 12b

```
     ┌Gln┐  280         290         300         310
     │CAG│   |           |           |           |
CCA  │ATG│ GTT AAT TTA TTA CAC AAT GAA AAT ATA ATT CCA GGT ATT
Pro  │MET│ Val Asn Leu Leu His Asn Glu Asn Ile Ile Pro Gly Ile
     └───┘
       ▲
      320                 340         350         360
       |                   |           |           |
AAG GTT GAT AAA GGT TTG GTT AAC ATT CCA TGC ACA GAT GAA GAA
Lys Val Asp Lys Gly Leu Val Asn Ile Pro Cys Thr Asp Glu Glu

370    ┌Cys┐ 380         390         400
          |     │TGT│  |           |           |
AAA TCA ACT CAA │GGT│ TTA GAT GGA TTA GCA GAA AGA TGC AAA GAG
Lys Ser Thr Gln │Gly│ Leu Asp Gly Leu Ala Glu Arg Cys Lys Glu
                └───┘
                  ▲
 410         420         430         440         450
  |           |           |           |           |
TAT TAT AAA GCT GGT GCA AGG TTT GCT AAA TGG AGA ACA GTT TTA
Tyr Try Lys Ala Gly Ala Arg Phe Ala Lys Trp Arg Thr Val Leu 460         470         480         490
       |           |           |           |
GTT ATT GAC ACA GCC AAA GGA AAA CCA ACT GAT TTA TCA AAT CAC
Val Ile Asp Thr Ala Lys Gly Lys Pro Thr Asp Leu Ser Asn His 500         510         520         530         540
  |           |           |           |           |
GAA ACT GCA TGG GGA TTG GCT AGA TAT GCA TCT ATT TGT CAA CAA
Glu Thr Ala Trp Gly Leu Ala Arg Tyr Ala Ser Ile Cys Gln Gln 550         560         570         580
       |           |           |           |
AAT AGA TTA GTT CCA ATT GTT GAA CCT GAA ATT TTA GCT GAT GGA
Asn Arg Leu Val Pro Ile Val Glu Pro Glu Ile Leu Ala Asp Gly
```

FIG. 12c

```
          590              600        610  RO-33 620              630
           |                |          |    ┌─→    |                |
      CCA CAC TCA ATT GAA GTT │TGC│ GCA GTT GTA ACT CAA AAA GTT TTA
                              │TGT│
      Pro His Ser Ile Glu Val Cys Ala Val Val Thr Gln Lys Val Leu
                              ▲         ●
          640              650        660              670
           |                |          |                |
      TCA TGT GTA TTT AAA GCT TTA CAA GAA AAT GGT GTA TTA TTA GAA
      Ser Cys Val Phe Lys Ala Leu Gln Glu Asn Gly Val Leu Leu Glu 680              690        700        710        720
           |                |          |          |          |
      GGT GCA TTG TTA AAA CCA AAC ATG GTT ACT GCT GGT TAT GAA TGT
      Gly Ala Leu Leu Lys Pro Asn MET Val Thr Ala Gly Tyr Glu Cys 730        740        750              760
                |          |          |                |
      ACT GCT AAA ACC ACT ACT CAA GAT GTT GGT TTC TTA ACT GTC AGA
      Thr Ala Lys Thr Thr Thr Gln Asp Val Gly Phe Leu Thr Val Arg 770        780        790        800        810
           |          |          |          |          |
      ACC TTA AGG AGA ACT GTA CCA CCA GCC TTA CCA GGT GTT GTA TTT
      Thr Leu Arg Arg Thr Val Pro Pro Ala Leu Pro Gly Val Val Phe 820        830        840        850
                |          |          |          |
      TTA TCT GGA GGA CAA TCA GAA GAA GAG GCT TCT GTT AAT TTA AAT
      Leu Ser Gly Gly Gln Ser Glu Glu Glu Ala Ser Val Asn Leu Asn 860        870        880        890        900
           |          |          |          |          |
      TCA ATC AAT GCT TTG GGT CCA CAC CCA TGG GCT TTA ACC TTC TCT
      Ser Ile Asn Ala Leu Gly Pro His Pro Trp Ala Leu Thr Phe Ser
```

FIG. 12d

```
          910           920           930           940
           |             |             |             |
TAC GGT AGA GCT TTA CAA GCT TCA GTA TTG AAC ACA TGG CAA GGA
Tyr GLy Arg Ala Leu Gln Ala Ser Val Leu Asn Thr Trp Gln Gly
          950           960           970           980           990
           |             |             |             |             |
AAG AAA GAA AAT GTT GCA AAG GCA AGA GAA GTT TTA TTA CAA AGA
Lys Lys Glu Asn Val Ala Lys Ala Arg Glu Val Leu Leu Gln Arg
          1000          1010          1020          1030
           |             |             |             |
GCT GAA GCC AAC TCC TTA GCA ACT TAT GGT AAA TAC AAA GGA GGT
Ala Glu Ala Asn Ser Leu Ala Thr Try Gly Lys Tyr Lys Gly Gly
          1040          1050          1060          1070          1080
           |             |             |             |             |
GCA GGT GGT GAA AAT GCA GGT GCT TCA TTA TAT GAA AAG AAA TAT
Ala Gly Gly Glu Asn Ala Gly Ala Ser Leu Tyr Glu Lys Lys Tyr

GTC TAT TAAAAACTTCACCAACCAAAAATGAATAATAATAATAATAAATAAATTAC
Val Tyr ■ ——————————————————— M 25 ▶ ———————

TAAATGAATGGTACTATATTTTTAAAAATAAGGGTAATATATTTTCTGTATGTATATAT
————————————AAATTATCCTTATACATGAACCATGTAACCATAAATTAAAATAT

ATATATATATATACAAAATATGTGAAATTATAAAAAAAAAAAAAAAAAAAAAAAAGGAAT
TTACATGAACATGTACATAAATT
         ◀┘M 25
```

1

RECOMBINANT MALARIAL POLYPEPTIDES

TECHNICAL FIELD

This invention relates to recombinant malarial polypeptides having epitopes of the *Plasmodium falciparum* merozoite antigen, and to such polypeptides which are covalently linked to affinity peptides.

BACKGROUND OF THE INVENTION

Malaria in human beings is caused by four species of Plasmodium, *P. falciparum, P. vivax, P. ovale* and *P. malariae*. According to a 1986 report of the World Health Organization (WHO). there are almost 100 million cases of malaria infection worldwide. Of these about 1 million, mostly cases of young children who are infected with *P. falciparum*, are fatal. Because of the appearance of drug resistant parasites and insecticide resistant mosquito vectors, malaria is spreading. Thus, the Indian Health Authorities reported 100,000 cases of malaria in 1962 and 3 million cases, caused mainly by P. vivax, in 1980 (see Bruce-Chwatt, Essential Malariology, 2nd edition, Heinemann, London [1986]).

Recent technical advances have raised hopes that it would soon be possible to produce an antimalarial vaccine which would counteract the growing spread of the disease. Firstly, new methods in the development of malarial vaccines, e.g., the cloning of genes and their expression in microbial host organisms and the use of monoclonal antibodies for antigen identification, can be used. Secondly, long-term cultures of *P. falciparum* in human red blood cells (Trager et al., Science 193, 673-675 [1976]) have provided a ready source of material for the study of the malaria parasite. More recently, it has become possible to maintain all stages in the life cycle of the parasite in the laboratory (Ponnudurai et al., Trans. R. Soc Trop. Med. Hyg. 76, 812-818 [1982]; Mazier et al., Science 227 440-442 [1985]).

The natural life cycle of *P. falciparum* has three different stages. In the first stage, mosquitoes introduce sporozoites into the blood vessels of vertebrates during the intake of food. These sporozoites travel via the bloodstream to the liver and invade the hepatocytes of the host. In the second stage, merozoites develop from these sporozoites. These merozoites pass through several multiplication cycles in erythrocytes of the host and then develop to gametocytes. The gametocytes, which are the sexual stage of the parasite, are taken up by mosquitoes when they feed. After fertilization in the stomach of the insect, the gametocytes develop into sporozoites which then travel to the salivary glands of the insect. There, the cycle can begin again.

Sporozoites, merozoites and gametocytes have different antigens. Vaccines can be produced in principle against any of the different stages of the malaria parasite, but it is known that many polypeptides of the parasite are genetically polymorphic, i.e. that the polypeptide changes slightly from generation to generation. This hinders the immunization of vertebrates against malaria using these polypeptides as antigens, since the once-formed antibodies in time can no longer recognize the altered antigens. Accordingly, an ideal vaccine would be one which is directed against a polypeptide of the parasite having an amino acid sequence which is not variable, i.e. against a polypeptide which is genetically stable. It is known that the amino acid sequence (primary structure) of polypeptides which carry out a specific function, such as enzymes, is constant at least in those regions of the primary structure which are important for function.

An example of a genetically stable polypeptide of *P. falciparum* is the merozoite antigen having the amino acid sequence (I):

MetAsnAlaProLysLysLeuProAlaAsPValAlaGlu-
GluLeuAlaThrThrAla-W-LysLeuValGlnAla-
GlyLysGlyIleLeuAlaAlaAspGluSerThrGlnThrIle-
Lys LysArgPheAspAsnIleLysLeuGluAsnThrIle-
GluAsnArgAlaSerTyrArgAsp LeuLeuPheGlyTh-
rLysGlyLeuGlyLysPheIleSerGlyAlaIleLeuPheGlu-
Glu ThrLeuPheGlnLysAsnGluAlaGlyValPro-X-
ValAsnLeuLeuHisAsnGluAsn IleIleProGlyIleLys-
ValAspLys-Y-LeuValAsnIleProCysThrAspGluGlu
LysSerThrGln-Z-LeuAspGlyLeuAlaGluArgCys-
LysGluTyrTyrLysAlaGly AlaArgPheAlaLysT-
rpArgThrValLeuValIleAspThrAlaLysGlyLys-
ProThr AspLeuSerAsnHisGluThrAlaTrp-
GlyLeuAlaArgTyrAlaSerIleCysGlnGln AsnAr-
gLeuValProIleValGluProGluIleLeuAlaAspGly-
ProHisSerIleGlu ValCysAlaValValThrGlnLysVal-
LeuSerCysValPheLysAlaLeuGlnGluAsn GlyVal-
LeuLeuGluGlyAlaLeuLeuLysProAsnMetVal-
ThrAlaGlyTyrGluCys ThrAlaLysThrThrThrGl-
nAspValGlyPheLeuThrValArgThrLeuArgArgThr
ValProProAlaLeuProGlyValValPheLeuSerGly-
GlyGlnSerGluGluGluAla SerValAsnLeuAsn-
SerIleAsnAlaLeuGlyProHisProTrpAlaLeuThr-
PheSer TyrGlyArgAlaLeuGlnAlaSerVal-
LeuAsnThrTrpGlnGlyLysLysGluAsnVal
AlaLysAlaArgGluValLeuLeuGlnArgAla-
GluAlaAsnSerLeuAlaThrTyrGly LysTyrLysGly-
GlyAlaGlyGlyGluAsnAlaGlyAlaSerLeuTyr-
GluLysLysTyr ValTyr wherein —W— is Gln or can be absent;
—X— is Met or Gln;
—Y— is Gly or Cys and
—Z— is Gly or Cys.

BRIEF DESCRIPTION OF THE FIGURES

The following Figures and the detailed Example below will facilitate better understanding of the present invention. However, the invention is not limited by the Example or by the Figures, which are offered by way of illustration only.

B, Bg, E, H, Sa, X and Xb denote cleavage sites for the restriction enzymes BamHI, BglII, EcoRI, HindIII, SalI, XhoI and XbaI, respectively.

▨ represents the promoters of the genes bla, lacI and neo; ▤ represents the ribosomal binding sites of the genes bla, cat, neo and lacI; ▥ represents the terminators $t_o$ and $T_1$; ▨ represents the regulatable promoter/operator element N25OPSN25OP29; ▤ represents the ribosomal binding site RBSII; → represents the coding r control of this ribosomal binding site; ▨ represents a region which codes for the six histidines; ⇌ represents the region which is required for replication (repl.); ■ represents coding regions for dihydrofolate reductase (dhfr), chloramphenicol acetyltransferase (cat), lac repressor (lacI), β-lactamase (bla) and neomycin phosphotransferase (neo).

BRIEF DESCRIPTION OF THE DRAWINGS

Figure 1:
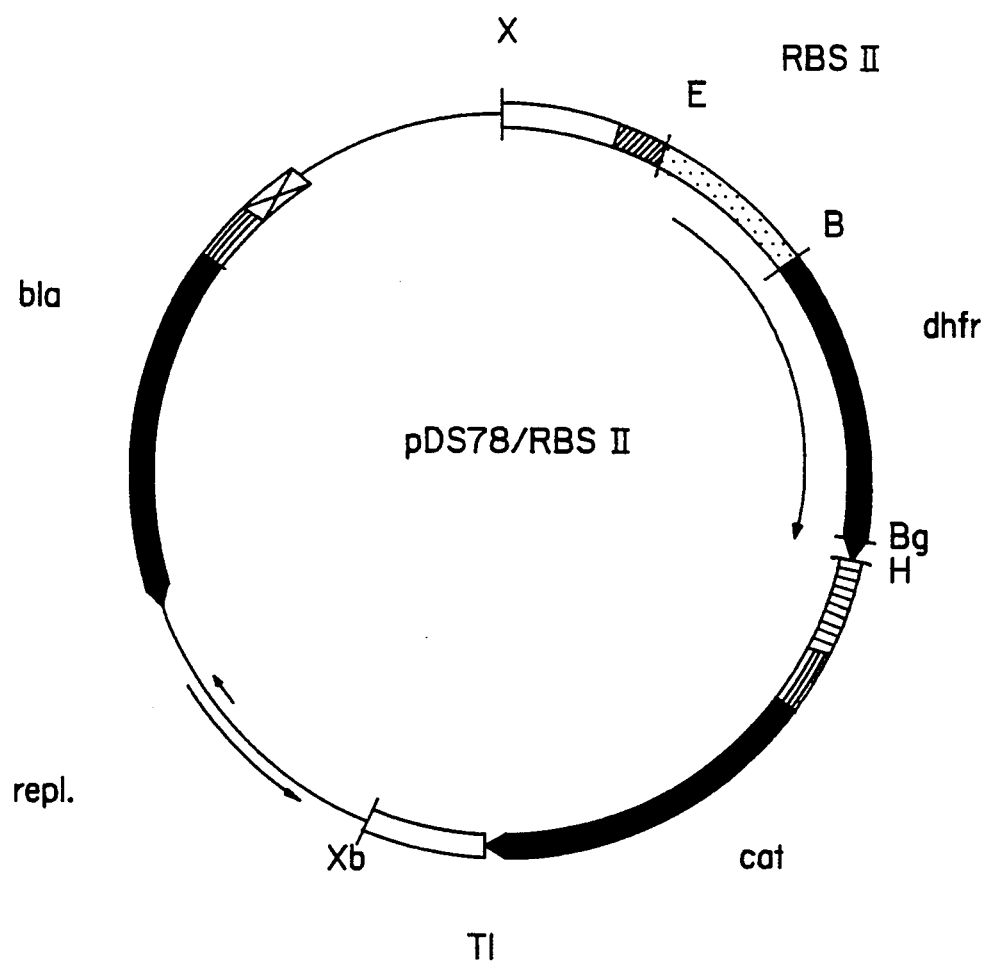

FIG. 1 Schematic representation of the plasmid pDS78/RBSII.

FIG. 2(a) through 2(d) Nucleotide sequence of the plasmid pDS78/RBSII. In the sequence the recognition sites for the restriction enzymes set forth in FIG. 1 are overlined, while the regions coding for β-lactamase and dihydrofolate reductase are underlined.

Figure 3:
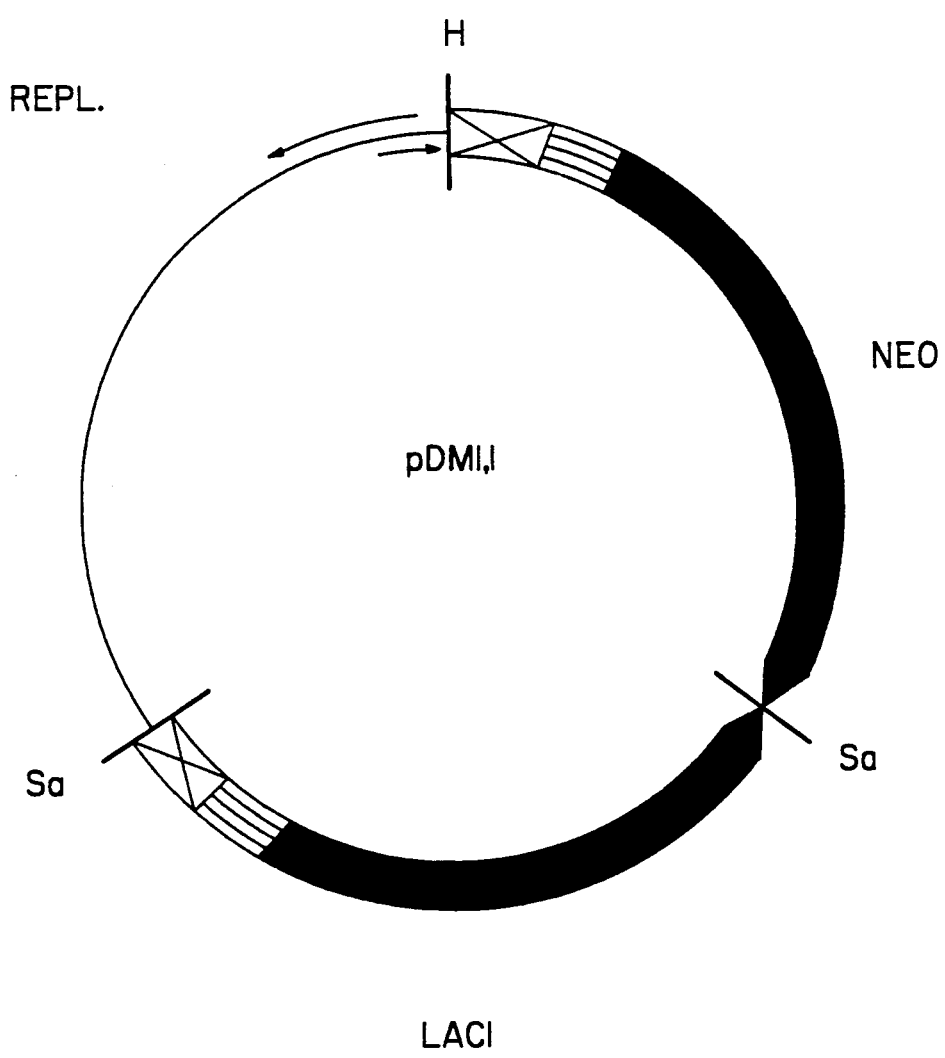

FIG. 3 Schematic representation of the plasmid pDMI,1.

FIG. 4(a) through 4(c) Nucleotide sequence of the plasmid pDMI,1. In the sequence the recognition sites for the restriction enzymes set forth in FIG. 3 are overlined, while the regions coding for neomycin phosphotransferase and lac repressor are underlined.

Figure 5:
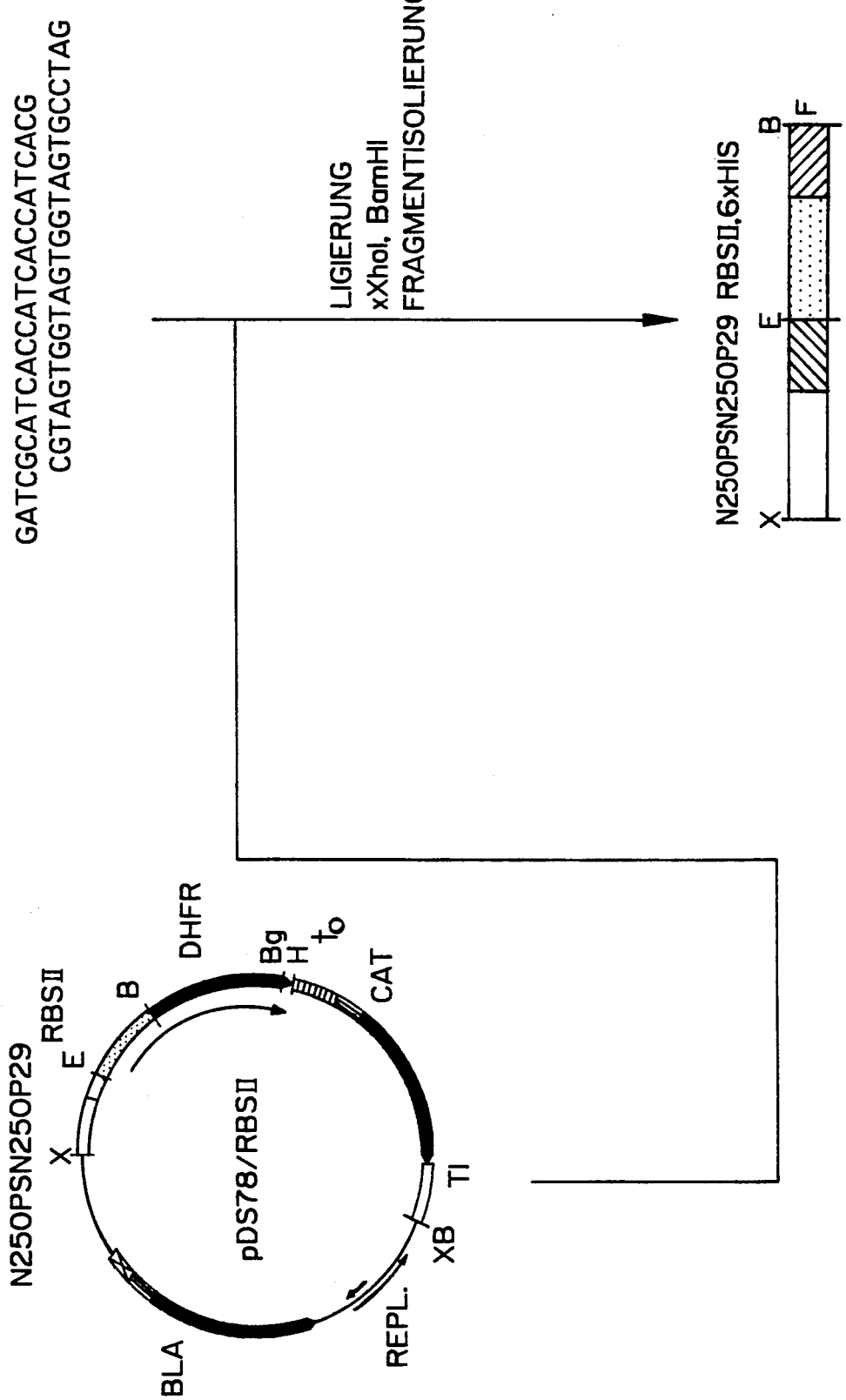

FIG. 5 Schematic representation of the production of the XhoI/BamHI fragment having the regulatable promoter/operator element N25OPSN25OP29, the ribosomal binding site RBSII and the region coding for six histidines.

Figure 6:
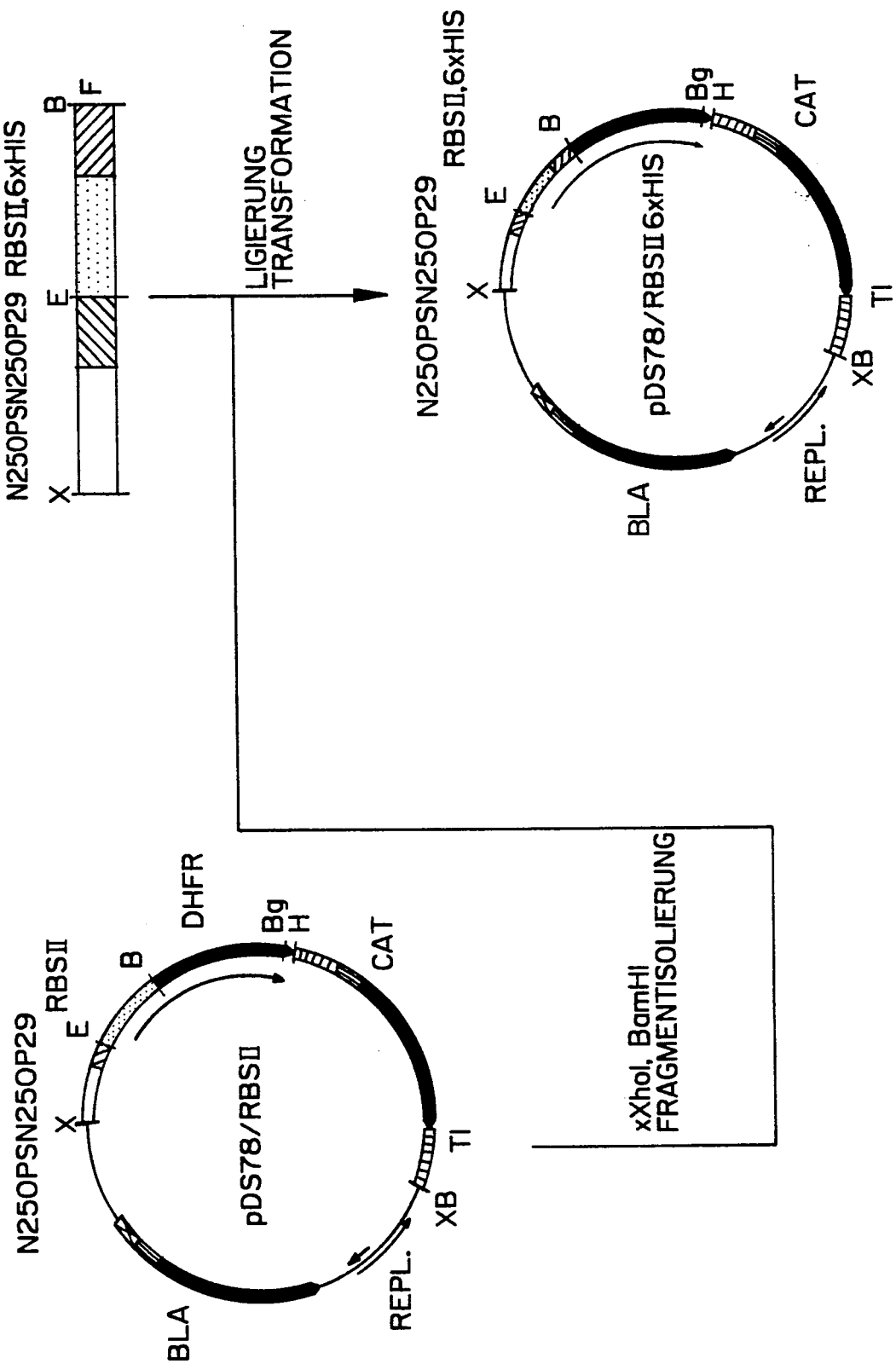

FIG. 6 Schematic representation of the construction of the plasmid pDS78/RBSII,6xHis using the plasmids pDS78/RBSII and the XhoI/BamHI fragment F having the regulatable promoter/operator element N25OPSN25OP29, the ribosomal binding site RBSII and the region coding for six histidines.

Figure 7:
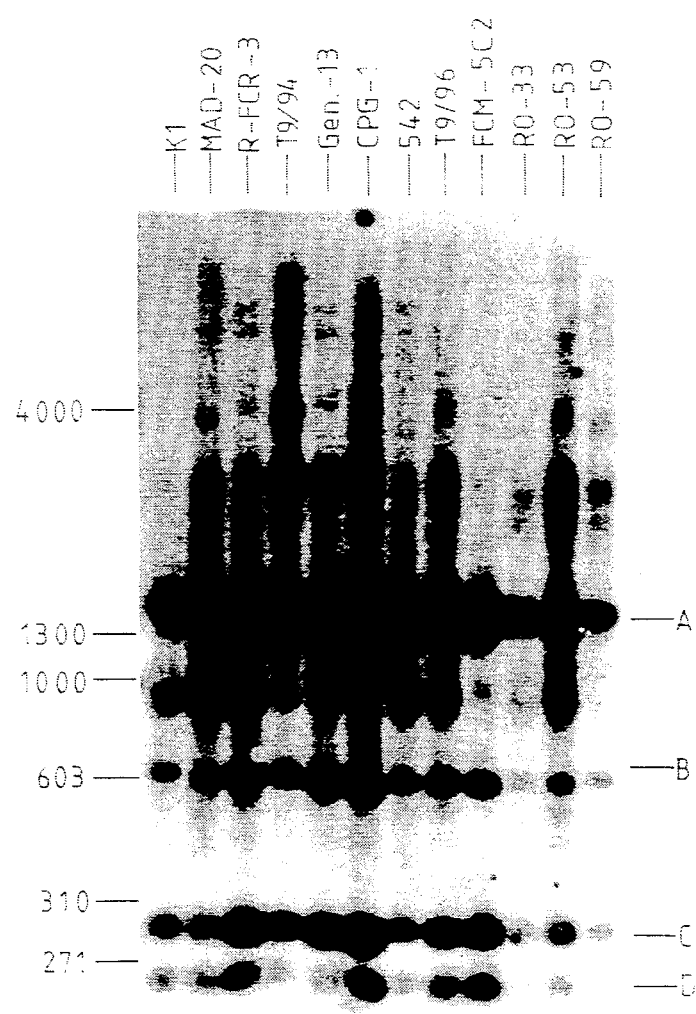

FIG. 7 Southern Transfer Analysis (Southern, J. Mol. Biol. 98, 503-517 [1975] of genomic DNA from 12 different strains of P. falciparum. All 12 isolates have the typical DraI fragments. The P. falciparum DNA fragment from Kl-B served as the probe.

FIG. 8 Western Transfer Analysis (Western blot, Towbin et al., Proc. Natl. Acad. Sci. USA, 76, 4350-4354 [1979]) of P. falciparum proteins from 11 isolates having antibodies against the merozoite antigen of P. falciparum. All 11 isolates have the characteristic bands which correspond to a polypeptide having a molecular weight of about 41,000.

Figure 9:
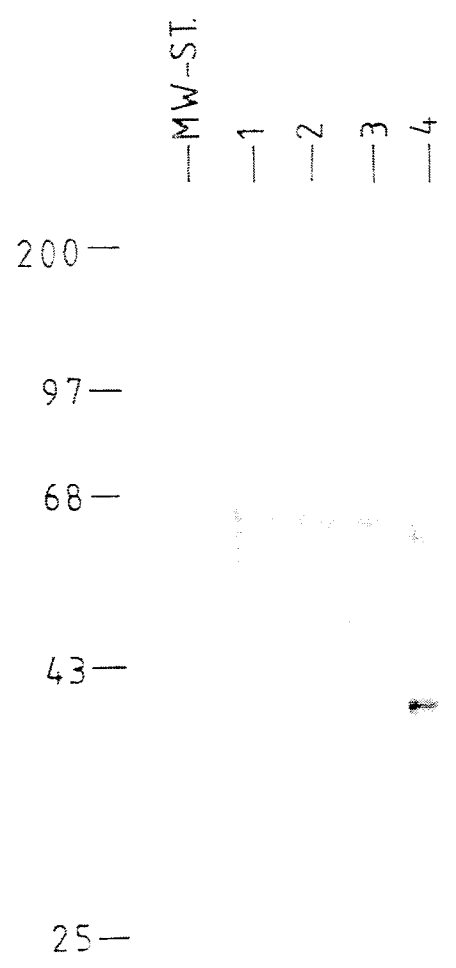

FIG. 9 Expression of the recombinant protein (27 kD) in E. coli E. coli cell lysates were tested in the Western blot with antibodies against the parasite antigen. The trace denoted as MW-ST contains pre-stained molecular weight standard. The size is given in kilodaltons (1,000 Daltons). Trace 1 contains a non-induced lysate of the transformed cells. Trace 2 contains an induced probe. Trace 3 contains non-transformed cells as the control. Trace 4 contains a P. falciparum Kl lysate. As expected the antibodies react only with the recombinant protein (27 kD) in Trace 2 and with the parasite protein (41 kD) in Trace 4.

FIG. 10 Purification of the recombinant protein (41 kD) Analytical polyacrylamide gel electrophoreses and Western blot analysis of the various purification steps in the purification of the recombinant protein (41 kD). (A) Polyacrylamide gel stained with Coomassie blue. Trace 1: Cell lysate of E. coli cells transformed with p8/3. Trace 2: Soluble fraction of the cell lysate after centrifugation (100,000×g). Trace 3: Eluate of the material bonded specifically to the phosphocellulose column. Trace 4: Eluate of the material bonded specifically to the NTA resin. Trace 5: End product after ultrafiltration on a Sephacryl TM S-200 column. The following molecular weight marker proteins were used: 31=carboanhydrase molecular weight (MW)=31,000 Dalton, 45=ovalbumin MW=45,000 Dalton, 66=bovine serum albumin MW=66,000 Dalton, 92=phosphorylase B MW=92,000 Dalton. (B) Western blot of polyacrylamide gel (A) with rabbit antiserum against an E. coli lysate. (C) Western blot of the polyacrylamide gel (A) with antibodies against merozoite antigens of P. falciparum (Perrin et al., J. Clin. Invest. 75, 1718-1721 [1985]).

FIGS. 11(a) through 11(e) Nucleotide sequence of the plasmid p8/3 The sequence which codes for the polypeptide (41 kD) begins with the ATG at position 115-117 (S) and ends with the stop codon at position 1255-1257 (T). The sequence which codes for the affinity peptide begins with the aforementioned ATG and ends with the tyrosine (Tyr) coding codon TAT at position 166-168, while the sequence coding for the partial sequence B of the polypeptide (4I kD) begins with the codon ATG at position 169-171 whih codes for methionine (Met) and likewise ends with the stop codon at position 1255-1257.

FIG. 12(a) through 12(d) Nucleotide sequence and the amino acid sequence derived therefrom of the genomic DNA of the P. falciparum Kl isolate which codes for the 41,000 Dalton merozoite antigen. The N-terminal Met is underlined. The open reading frame ends with the termination codon TAA at position 1087 to 1089. The Figure also shows a part of the non-coding sequence prior to and after the sequence coding for the merozoite antigen. The nucleotide sequence of the genomic DNA of another isolate (RO-33, Ghana) was largely identical with the nucleotide sequence from the Kl isolate. M25 denotes the corresponding nucleotide sequence of a cDNA of the M25 isolate from P. falciparum. The nucleotide sequences differ in the coding sequence in 3 codons which are framed in FIG. 12. The differences in the sequences lead to two amino acid exchanges, with a Met or a Gly in the merozoite antigen of the Kl isolate corresponding to a Gln or a Cys in the merozoite antigen of the M25 isolate.

DESCRIPTION OF THE INVENTION

The present invention provides polypeptides which correspond in at least one specific epitope with the Plasmodium falciparum merozoite antigen having the amino acid sequence (I). A specific epitope is an immunogenic determinant on a polypeptide which is formed by a specific molecular configuration of a partial sequence of the polypeptide. The invention also provides polypeptides as defined above which, in addition, are covalently linked to an affinity peptide.

Affinity peptides contain sequences of amino acid residues which bind preferably to affinity chromatography carrier materials. Examples of such affinity peptide residues are peptide residues which contain at least two histidine residues. Such affinity peptide residues bind selectively to nitrilotriacetic acid-nickel chelate resins (see, e.g., European Patent Application, Publ. No. 253 303). Polypeptides which contain such an affinity peptide residue can be separated selectively from the remaining polypeptides by means of such resins. The affinity peptide can be linked either with the C-terminus or the N-terminus of the polypeptide defined above, but the linkage is preferably with the N-terminus, especially when the natural stop codon of the malaria antigen is utilized in the expression of the polypeptide in accordance with the invention.

The preferred polypeptide in accordance with the present invention can be represented by the general formula

A-B wherein
A is an affinity peptide or can be absent

B is a polypeptide which corresponds in at least one specific epitope with the *P. falciparum* merozoite antigen having the amino acid sequence (I).

The most preferred polypeptides in accordance with the invention have the amino acid sequence: MetArgGlySerHisHisHisHisHisHisGlySerGlyAsnIleProCysThrAspGlu GluLysSerThrGlnGlyLeuAspGlyLeuAlaGluArgCysLysGluTyrTyrLysAla GlyAlaArgPheAlaLysTrpArgThrValLeuValIleAspThrAlaLysGlyLysPro ThrAspLeuSerAsnHisGluThrAlaTrpGlyLeuAlaArgTyrAlaSerIleCysGln GlnAsnArgLeuValProIleValGluProGluIleLeuAlaAspGlyproHisSerIle GluValCysAlaValValThrGlnLysValLeuSerCysValPheLysAlaLeuGlnGlu AsnGlyValLeuLeuGluGlyAlaLeuLeuLysProAsnMetValThrAlaGlyTyrGlu CysThrAlaLysThrThrThrGlnAspValGlyPheLeuThrValArgThrLeuArgArg ThrValProProAlaLeuProGlyValValPheLeuSerGlyGlyGlnSerGluGluGlu AlaSerValAsnLeuAsnSerIleAsnAlaLeuGlyProHisProTrpAlaLeuThrPhe SerTyrGlyArgAlaLeuGlnAlaSerValLeuAsnThrTrpGlnGlyLysLysGluAsn ValAlaLysAlaArgGluValLeuLeuGlnArgAlaGluAlaAsnSerLeuAlaThrTyr GlyLysTyrLysGlyGlyAlaGlyGlyGluAsnAlaGlyAlaSerLeuTyrGluLysLys TyrValTyr (II), MetArgGlySerHisHisHisHisHisHisGlySerGlyAsnIleProCysThrAspGlu GluLysSerThrGlnCysLeuAspGlyLeuAlaGluArgCysLysGluTyrTyrLysAla GlyAlaArgPheAlaLysTrpArgThrValLeuValIleAspThrAlaLysGlyLysPro ThrAspLeuSerAsnHisGluThrAlaTrpGlyLeuAlaArgTyrAlaSerIleCysGln GlnAsnArgLeuValProIleValGluProGluIleLeuAlaAspGlyProHisSerIle GluValCysAlaValValThrGlnLysValLeuSerCysValPheLysAlaLeuGlnGlu AsnGlyValLeuLeuGluGlyAlaLeuLeuLysProAsnMetValThrAlaGlyTyrGlu CysThrAlaLysThrThrThrGlnAspValGlyPheLeuThrValArgThrLeuArgArg ThrValProProAlaLeuProGlyValValPheLeuSerGlyGlyGlnSerGluGluGlu AlaSerValAsnLeuAsnSerIleAsnAlaLeuGlyProHisProTrpAlaLeuThrPhe SerTyrGlyArgAlaLeuGlnAlaSerValLeuAsnThrTrpGlnGlyLysLysGluAsn ValAlaLysAlaArgGluValLeuLeuGlnArgAlaGluAlaAsnSerLeuAlaThrTyr GlyLysTyrLysGlyGlyAlaGlyGlyGluAsnAlaGlyAlaSerLeuTyrGluLysLys TyrValTyr (II'), MetArgGlySerHisHisHisHisHisHisGlySerGluLeuAlaCysGlnTyrMetAsn AlaProLysLysLeuProAlaAspValAlaGluGluLeuAlaThrThrAlaLysLeuVal GlnAlaGlyLysGlyIleLeuAlaAlaAspGluSerThrGlnThrIleLysLysArgPhe AspAsnIleLysLeuGluAsnThrIleGluAsnArgAlaSerTyrArgAspLeuLeuPhe GlyThrLysGlyLeuGlyLysPheIleSerGlyAlaIleLeuPheGluGluThrLeuPhe GlnLysAsnGluAlaGlyValProGlnValAsnLeuLeuHisAsnGluAsnIleIlePro GlyIleLysValAspLysCysLeuValAsnIleProCysThrAspGluGluLysSerThr GlnGlyLeuAspGlyLeuAlaGluArgCysLysGluTyrTyrLysAlaGlyAlaArgPhe AlaLysTrpArgThrValLeuValIleAspThrAlaLysGlyLysProThrAspLeuSer AsnHisGluThrAlaTrpGlyLeuAlaArgTyrAlaSerIleCysGlnGlnAsnArgLeu ValProIleValGluProGluIleLeuAlaAspGlyProHisSerIleGluValCysAla ValValThrGlnLysValLeuSerCysValPheLysAlaLeuGlnGluAsnGlyValLeu LeuGluGlyAlaLeuLeuLysProAsnMetValThrAlaGlyTyrGluCysThrAlaLys ThrThrThrGlnAspValGlyPheLeuThrValArgThrLeuArgArgThrValProPro AlaLeuProGlyValValPheLeuSerGlyGlyGlnSerGluGluGluAlaSerValAsn LeuAsnSerIleAsnAlaLeuGlyProHisProTrpAlaLeuThrPheSerTyrGlyArg AlaLeuGlnAlaSerValLeuAsnThrTrpGlnGlyLysLysGluAsnValAlaLysAla ArgGluValLeuLeuGlnArgAlaGluAlaAsnSerLeuAlaThrTyrGlyLysTyrLys GlyGlyAlaGlyGlyGluAsnAlaGlyAlaSerLeuTyrGluLysLysTyrValTyr (III), MetArgGlySerHisHisHisHisHisHisGlySerGluLeuAlaCysGlnTyrMetAsn AlaProLysLysLeuProAlaAspValAlaGluGluLeuAlaThrThrAlaGlnLysLeu ValGlnAlaGlyLysGlyIleLeuAlaAlaAspGluSerThrGlnThrIleLysLysArg PheAspAsnIleLysLeuGluAsnThrIleGluAsnArgAlaSerTyrArgAspLeuLeu PheGlyThrLysGlyLeuGlyLysPheIleSerGlyAlaIleLeuPheGluGluThrLeu PheGlnLysAsnGluAlaGlyValProGlnValAsnLeuLeuHisAsnGluAsnIleIle ProGlyIleLysValAspLysGlyLeuValAsnIleProCysThrAspGluGluLysSer ThrGlnGlyLeuAspGlyLeuAlaGluArgCysLysGluTyrTyrLysAlaGlyAlaArg PheAlaLysTrpArgThrValLeuValIleAspThrAlaLysGlyLysProThrAspLeu SerAsnHisGluThrAlaTrpGlyLeuAlaArgTyrAlaSerIleCysGlnGlnAsnArg LeuValProIleValGluProGluIleLeuAlaAspGlyProHisSerIleGluValCys AlaValValThrGlnLysValLeuSerCysValPheLysAlaLeuGlnGluAsnGlyVal LeuLeuGluGlyAlaLeuLeuLysProAsnMetValThrAlaGlyTyrGluCysThrAla LysThrThrThrGlnAspValGlyPheLeuThrValArgThrLeuArgArgThrValPro ProAlaLeuProGlyValValPheLeuSerGlyGlyGlnSerGluGluGluAlaSerVal AsnLeuAsnSerIleAsnAlaLeuGlyProHisProTrpAlaLeuThrPheSerTyrGly ArgAlaLeuGlnAlaSerValLeuAsnThrTrpGlnGlyLysLysGluAsnValAlaLys AlaArgGluValLeuLeuGlnArgAlaGluAlaAsnSerLeuAlaThrTyrGlyLysTyr LysGlyGlyAlaGlyGlyGluAsnAlaGlyAlaSerLeuTyrGluLysLysTyrValTyr (III'), MetArgGlySerHisHisHisHisHisHisGlySerGluLeuAlaCysGlnTyrMetAsn AlaProLysLysLeuProAlaAspValAlaGluGluLeuAlaThrThrAlaGlnLysLeu ValGlnAlaGlyLysGlyIleLeuAlaAlaAspGluSerThrGlnThrIleLysLysArg PheAspAsnIleLysLeuGluAsnThrIleGluAsnArgAlaSerTyrArgAspLeuLeu PheGlyThrLysGlyLeuGlyLysPheIleSerGlyAlaIleLeuPheGluGluThrLeu PheGlnLysAsnGluAlaGlyValProMetValAsnLeuLeuHisAsnGluAsnIleIle ProGlyIleLysValAspLysGlyLeuValAsnIleProCysThrAspGluGluLysSer ThrGlnGlyLeuAspGlyLeuAlaGluArgCysLysGluTyrTyrLysAlaGlyAlaArg PheAlaLysTrpArgThrValLeuValIleAspThrAlaLysGlyLysProThrAspLeu SerAsnHisGluThrAlaTrpGlyLeuAlaArgTyrAlaSerIleCysGlnGlnAsnArg LeuValProIleValGluProGluIleLeuAlaAspGlyProHisSerIleGluValCys AlaValValThrGlnLysValLeuSerCysValPheLysAlaLeuGlnGluAsnGlyVal LeuLeuGluGlyAlaLeuLeuLysProAsnMetValThrAlaGlyTyrGluCysThrAla LysThrThrThrGlnAspValGlyPheLeuThrValArgThrLeuArgArgThrValPro ProAlaLeuProGlyValValPheLeuSerGlyGlyGlnSerGluGluGluAlaSerVal AsnLeuAsnSerIleAsnAlaLeuGlyProHisProTrpAlaLeuThrPheSerTyrGly ArgAlaLeuGlnAlaSerValLeuAsnThrTrpGlnGlyLysLysGluAsnValAlaLys AlaArgGluValLeuLeuGlnArgAlaGluAlaAsnSerLeuAlaThrTyrGlyLysTyr LysGlyGlyAlaGlyGly GluAsnAlaGlyAlaSerLeuTyrGluLysLysTyrVal-Tyr (III″).

MetArgGlySerHisHisHisHisHisHisGlySer-GluLeuAlaCysGlnTyrMetAsn AlaProLysLysLeu-ProAlaAspValAlaGluGluLeuAlaThrThrAlaGl-nLysLeu ValGlnAlaGlyLysGlyIleLeuAlaAlaAsp-GluSerThrGlnThrIleLysLysArg PheAspAsnIleLys-LeuGluAsnThrIleGluAsnArgAlaSerTyrArgAs-pLeuLeu PheGlyThrLysGlyLeuGlyLysPheIleSer-GlyAlaIleLeuPheGluGluThrLeu PheGlnLysAsn-GluAlaGlyValProGlnValAsnLeuLeuHisAsn-GluAsnIleIle ProGlyIleLysValAspLys-GlyLeuValAsnIleProCysThrAspGluGluLysSer ThrGlnCysLeuAspGlyLeuAlaGluArgCysLys-GluTyrTyrLysAlaGlyAlaArg PheAlaLysT-rpArgThrValLeuValIleAspThrAlaLysGlyLysPro-ThrAspLeu SerAsnHisGluThrAlaTrp-GlyLeuAlaArgTyrAlaSerIleCysGlnGlnAsnArg LeuValProIleValGluProGluIleLeuAlaAspGly-ProHisSerIleGluValCys AlaValValThrGlnLysVal-LeuSerCysValPheLysAlaLeuGlnGluAsnGlyVal LeuLeuGluGlyAlaLeuLeuLysProAsnMetVal-ThrAlaGlyTyrGluCysThrAla LysThrThrThrGl-nAspValGlyPheLeuThrValArgThrLeuArgArgTh-rValPro ProAlaLeuProGlyValValPheLeuSerGly-GlyGlnSerGluGluGluAlaSerVal AsnLeuAsn-SerIleAsnAlaLeuGlyProHisProTrpAlaLeuThr-PheSerTyrGly ArgAlaLeuGlnAlaSerVal-LeuAsnThrTrpGlnGlyLysLysGluAsnValAlaLys AlaArgGluValLeuLeuGlnArgAlaGluAlaAsnSer-LeuAlaThrTyrGlyLysTyr LysGlyGlyAlaGlyGly-GluAsnAlaGlyAlaSerLeuTyrGluLysLysTyrVal-Tyr (III‴), or

MetArgGlySerHisHisHisHisHisHisGlySer-GluLeuAlaCysGlnTyrMetAsn AlaProLysLysLeu-ProAlaAspValAlaGluGluLeuAlaThrThrAlaGl-nLysLeu ValGlnAlaGlyLysGlyIleLeuAlaAlaAsp-GluSerThrGlnThrIleLysLysArg PheAspAsnIleLys-LeuGluAsnThrIleGluAsnArgAlaSerTyrArgAs-pLeuLeu PheGlyThrLysGlyLeuGlyLysPheIleSer-GlyAlaIleLeuPheGluGluThrLeu PheGlnLysAsn-GluAlaGlyValProMetValAsnLeuLeuHisAsn-GluAsnIleIle ProGlyIleLysValAspLys-GlyLeuValAsnIleProCysThrAspGluGluLysSer ThrGlnCysLeuAspGlyLeuAlaGluArgCysLys-GluTyrTyrLysAlaGlyAlaArg PheAlaLysT-rpArgThrValLeuValIleAspThrAlaLysGlyLysPro-ThrAspLeu SerAsnHisGluThrAlaTrp-GlyLeuAlaArgTyrAlaSerIleCysGlnGlnAsnArg LeuValProIleValGluProGluIleLeuAlaAspGly-ProHisSerIleGluValCys AlaValValThrGlnLysVal-LeuSerCysValPheLysAlaLeuGlnGluAsnGlyVal LeuLeuGluGlyAlaLeuLeuLysProAsnMetVal-ThrAlaGlyTyrGluCysThrAla LysThrThrThrGl-nAspValGlyPheLeuThrValArgThrLeuArgArgTh-rValPro ProAlaLeuProGlyValValPheLeuSerGly-GlyGlnSerGluGluGluAlaSerVal AsnLeuAsn-SerIleAsnAlaLeuGlyProHisProTrpAlaLeuThr-PheSerTyrGly ArgAlaLeuGlnAlaSerVal-LeuAsnThrTrpGlnGlyLysLysGluAsnValAlaLys AlaArgGluValLeuLeuGlnArgAlaGluAlaAsnSer-LeuAlaThrTyrGlyLysTyr LysGlyGlyAlaGlyGly-GluAsnAlaGlyAlaSerLeuTyrGluLysLysTyrVal-Tyr (III⁗).

The invention also provides polypeptides of the general formula A-B having an amino acid sequence derived from the amino acid sequences indicated above by additions, deletions, insertions or amino acid substitutions, provided that these polypeptides are still capable of eliciting an immune response against the merozoite stage of malaria parasites, preferably against the merozoite antigen having the amino acid sequence (I) of *P. falciparum*. The invention also provides DNA sequences which code for a polypeptide of the invention, and replicable microbial vectors which contain such DNA sequences, especially expression vectors i.e. replicable microbial vectors, in which a DNA sequence which codes for a polypeptide of the invention is operatively linked to an expression control sequence in such a way that the DNA sequence coding for the polypeptide can be expressed. Moreover, the present invention provides microorganisms which contain such a replicable vector or expression vector and a process for their production. Furthermore, the present invention provides a process for the production of the polypeptides and methods for their use for the immunization of mammals against malaria.

The amino acid sequences of the polypeptides of the invention can differ from the amino acid sequences given above by having certain amino acid substitutions which have no influence on spatial structure or biological activity. Examples of such amino acid substitutions are Ala/Ser, Val/Ile, Asp/Glu, Thr/Ser, Ala/Gly, Ala/Thr, Ser/Asn, Ala/Val, Ser/Gly Tyr/Phe, Ala/Pro, Lys/Arg, Asp/Asn, Leu/Ile, Leu/Val, Ala/Glu and vice versa (see Doolittle, in "The Proteins", Eds. Neurath, H, and Hill, R. L., Academic Press, New York [1979]).

The polypeptides can be covalently bound to a carrier material or can be adsorbed thereon. Suitable carrier materials are natural or synthetic polymeric compounds such as, e.g., copolymers of one or more amino acids (e.g., polysine) or sugars (e.g., polysaccharides). Other suitable carrier materials are natural polypeptides such as hemocyanins (e.g., KLH, or "keyhole limpet hemocyanin"), serum proteins (e.g., gammaglobulin, serum albumin) and toxoids (e.g., diphtheria or tetanus toxoid). Other suitable carrier materials are known to those skilled in the art.

The covalent bonding of the polypeptides of the invention to the carrier materials can be effected in a known manner, e.g., directly by the formation of a peptide or ester bond between free carboxyl, amino or hydroxyl groups of the polypeptide and the corresponding groups on the carrier material or indirectly by using conventional, bifunctional reagents such as m-maleimidobenzoyl-N-hydroxysuccinimide ester (MBS) or succinimidyl 4-(p-maleimidophenyl)butyrate (SMPB). These and other bifunctional reagents are commercially obtainable, e.g., from Pierce Chemical Company, Rockford, Ill. Furthermore, $C_{2-7}$-dialkanals, such as glutaraldehyde (Avrameas, Immunochem. 6, 43–52 [1969]), can be used.

The carrier materials to which the polypeptides are bonded can be separated from non-bonded polypeptides and if desired, from excess reagents by known methods (e.g., by dialysis or column chromatography).

The peptides can be produced by conventional methods of peptide synthesis in the liquid phase or, preferably, on the solid phase, such as the methods of Merrifield (J. Am. Chem. Soc. 85, 2149–2154 [1963]) or by other equivalent methods commonly used in the art.

Solid phase synthesis begins with the C-terminal amino acid of the peptide to be synthesized, which is coupled in protected form to an appropriate resin. The starting material can be produced by coupling an amino acid, which is protected at the amino group, to a chloromethylated or a hydroxymethylated resin via a benzyl ester bridge or via an amide bond to a benzhydrylamine (BHA) resin, a methylbenzhydrylamine (MBHA) resin or a benzyloxybenzyl alcohol resin. These resins are commercially obtainable and their production and use are well-known.

General methods for the protection and removal of protecting groups from amino acids, which can be used in this invention, are described in "The Peptides", Vol. 2 (edited by E. Gross and J. Meienhofer, Academic Press, New York, 1–284 [1979]). Protecting groups include, e.g., the 9-fluorenylmethyloxycarbonyl (Fmoc), the tertiary butyloxycarbonyl (Boc), the benzyl (Bzl), the t-butyl (But), the 2-chlorobenzyloxycarbonyl (2Cl-Z), the dichlorobenzyl (Dcb) and the 3,4-dimethylbenzyl (Dmb) group.

After removal of the α-amino protecting group, the protected amino acids are coupled stepwise in the desired sequence to the C-terminal amino acid bonded to the resin. The complete peptide can thus be synthesized. As an alternative thereto small peptides can be synthesized and then joined together to give the desired peptide. Suitable coupling reagents are well known in the art; dicyclohexylcarbodiimide (DCC) is especially preferred.

Each protected amino acid or peptide is added in excess to the solid phase synthesis reaction vessel and the coupling reaction can be carried out in dimethylformamide (DMF) or methylene chloride ($CH_2Cl_2$) or a mixture of both. In cases of incomplete coupling, the coupling reaction is repeated before the N-terminal α-amino protecting group is removed for the purpose of coupling the next amino acid. The yield of each coupling step can be followed, preferably according to the ninhydrin method. The coupling reactions and the washing steps can be carried out automatically.

Cleavage of the peptide from the carrier material can be achieved by methods which are well known in peptide chemistry, e.g., by reaction with hydrogen fluoride (HF) in the presence of p-cresol and dimethyl sulphide for 1 hour at 0° C., followed possibly by a second reaction with HF in the presence of p-cresol for 2 hours at 0° C. The cleavage of the peptides from chloromethylated or hydroxymethylated carrier materials gives peptides having a free C-terminus; the cleavage of peptides from benzylhydrylamine or methylbenzylhydrylamine carriers gives peptides having an amidated C-terminus.

Alternatively, the polypeptides of the invention can be produced using recombinant DNA technology (Manniatis et al., in "Molecular Cloning—A Laboratory Manual", Cold Spring Harbor Laboratory [1982]). For example, a DNA fragment which codes for a polypeptide can be synthesized by conventional chemical methods, e.g., by the phosphotriester method described by Narang et al. in Meth. Enyzmol. 68, 90–108 [1979], or by the phosphodiester method (Brown et al., Meth. Enzymol. 68, 109–151 [1979]). In both methods, long oligonucleotides ar first synthesized and then joined together in a predetermined way.

The nucleotide sequence of the DNA fragment can be identical to the nucleotide sequence which codes for the natural polypeptide in plasmodium parasites. Since the genetic code is degenerate, however, there are many other sequences that can also code for the same polypeptide. The codons selected can be adapted to the preferred codon usage of the host used to express the gene coding for the recombinant polypeptide (Grosjean et al., Gene 18, 199–209 [1982]). Care must be taken that the DNA fragment used does not contain partial sequences which make the construction or use of the expression vector difficult, e.g., by introducing an undesired restriction enzyme cleavage site or by preventing the expression of the polypeptide.

Polypeptides of the general formula A-B can also be produced by isolating a DNA fragment which codes for the partial sequence B from the genome of a plasmodium isolate and expressing it in a host organism. The DNA fragment which codes for the partial sequence B can be obtained by cleaving genomic DNA of a Plasmodium strain with one or more suitable restriction endonucleases, e.g., EcoRl, Fragments with a length of 1.5 to $8 \times 10^3$ base pairs are isolated and inserted into a suitable vector, e.g., into the λ phage vector gtll (Young et al., Proc. Natl. Acad. Sci. USA 80, 1194–1198 [1983]) obtainable from the American Type Culture Collection, 12301 Parklawn Drive, Rockville, Md, USA (ATCC No. 37194).

The recombinant phage DNA can be packaged in phages in vitro. The thus-obtained phages are introduced into suitable host cells, e.g., into *E. coli* Y1088 containing the plasmid pMC9 (ATCC No. 37195). From about 100,000 recombinant phages there are selected those phages which hybridize with a suitable probe. Such suitable probes are oligonucleotides which correspond to a partial sequence of the genomic DNA coding for a polypeptide in accordance with the invention. The manner in which these probes are selected and used is well known in the art.

Phages which contain the desired DNA fragment are grown up and the DNA is isolated. Subsequently, the DNA fragment can be inserted into a suitable replicable microbial vector, preferably into an expression vector which provides the necessary expression signals and which codes for the partial sequence A of the general formula A-B of the polypeptides of the invention. The vector pDS78/RBSII,6xHis is a preferred expression vector. The construction and the production of this vector are described in detail in the Examples. The polypeptides of the present invention can, after corresponding adaptation of the nucleotide sequence, also be produced in other suitable expression vectors. Examples of such expression vectors are described in European Patent Application, Publication No. 186 069. Other expression vectors are known to those skilled in the art.

The expression vectors used to make the polypeptides of the invention are introduced into a suitable host organism. Suitable host organisms are microorganisms. e.g., yeast cells or bacterial cells which are capable of expressing polypeptides encoded by the expression vectors. The preferred host organism is *E. coli* M15 (described as DZ291 by Villarejo et al. in J. Bacteriol. 120, 466–474 [1974]). Other suitable host organisms are *E. coli* 294 (ATCC No. 31446), *E coli* RR1 (ATCC No. 31343) and *E. coli* W3110 (ATCC No. 27325).

The manner in which the expression of the polypeptides of the invention is carried out depends on the expression vector and on the host organism used. Usually, the host organisms which contain the expression vector are grown up under conditions which are optimal for the growth of the host organism. Towards the end of the exponential growth, when the increase in the number of cells per unit time decreases, the expression of the polypeptide is induced i.e. the DNA coding for the polypeptide is transcribed and the transcribed mRNA is translated. The induction can be effected by adding an inducer or a derepressor to the growth medium or by altering a physical parameter, e.g., by a temperature change. In the expression vector used in the example below, expression is controlled by the lac repressor. By adding isopropyl-β-D-thiogalactopyranoside (IPTG) the expression control sequence is derepressed and thereby the synthesis of the polypeptide is induced.

The polypeptide produced in the host organisms can be secreted from the cell by special transport mechanisms or can be isolated by breaking open the cell. The cell can be broken open by mechanical (Charm et al., Meth. Enzymol. 22, 476–556 [1971]), enzymatic (lysozyme treatment) or chemical (detergent treatment, urea or guanidine.HCl treatment, etc) means or by a combination thereof.

In eukaryotes, polypeptides which are secreted from the cell are synthesized in the form of a precursor molecule. The mature polypeptide results from cleavage of a so-called signal peptide. As prokaryotic host organisms are not capable of cleaving eukaryotic signal peptides from precursor molecules eukaryotic polypeptides must be expressed directly in their mature form in prokaryotic host organisms.

The translation start signal AUG, which corresponds to the codon ATG on the level of the DNA, causes all polypeptides synthesized in a prokaryotic host organism to have a methionine residue at the N-terminus. In certain expression systems, this N-teminal methionine residue is cleaved off. It has, however, been found that the presence or absence of the N-terminal methionine has no influence on the biological activity of a polypeptide (see Winnacker, in "Gene und Klone", p. 255, Verlag Chemie, Weinheim, BRD [1985]).

In cases where the N-terminal methionine is troublesome, it can also be cleaved off by means of a peptidase which is specific for the N-terminal methionine. Miller et al. (Proc. Natl. Acad. Sci. U.S.A. 84, 2718-2722 [1987] have described the isolation of such a peptidase from Salmonella typhimurium. The present invention is accordingly concerned with polypeptides with or without an N-terminal methionine residue.

The polypeptides of this invention can be purified by known methods such as differential centrifugation, precipitation with ammonium sulphate, dialysis (at normal pressure or at reduced pressure), preparative isoelectric focusing, preparative gel electrophoresis or various chromatographic methods such as gel filtration, high performance liquid chromatography (HPLC), ion exchange chromatography, reverse phase chromatography and affinity chromatography (e.g., on Sepharose ® blue CL-6B, on phosphocellulose, on carrier-bound monoclonal anti-bodies directed against the polypeptide or on metal chelate resins such as those described in the present invention).

The preferred purification method in the present invention is affinity chromatographic purification. The purification of the polypeptides on metal chelate resins (Sulkowsky, Trends in Biotechn. 3, 1-7 [1985]) or on phosphocellulose is especially preferred. The selective binding of neighbouring histidine residues to nitrilotriacetic acid-nickel chelate resins (NTA resins) and the affinity of aldolases to phosphocellulose are employed. These two purification methods can also be combined.

The polypeptides of the invention can be present in the form of multimers, e.g., in the form of dimers, trimers, tetramers, or can also be part of fusion polypeptides. Multimers can result when polypeptides are produced in prokaryotic host organisms, for example by the formation of disulphide bridges between cysteine residues. Fusion proteins can be produced by linking DNA fragments which code for a polypeptide of the present invention with one or more DNA fragments which code for another polypeptide. Examples of such a fusion polypeptide are polypeptides of the general formula A-B as defined above. Further examples are polypeptides of the general formula B-C or A-B-C in which C is another polypeptide and A and B have the significance given above, Examples of a polypeptide of the general formula A-B-C are, e.g., fusion polypeptides between Part B in the general formula A-B and β-galactosidase as can be produced in accordance with Rüther et al., EMBO J., 2, 1791-1794 [1983]. Neither the affinity peptide A nor the polypeptide C should be detrimental to the function of the polypeptides as antigens or as vaccines against malaria.

The present invention is also concerned with immunogenic compositions which contain a polypeptide of the invention and a suitable adjuvant. Suitable adjuvants for use in human beings and animals are well known in the art (WHO Techn. Rep Series 595, 1–40 [1976]; Jollis et al., "Chemical and Biological Basis of Adjuvants", in Molecular Biochemistry and Biophysics Vol. 13, 1-148 [1973], Springer Verlag Berlin).

The polypeptides of this invention can be present as lyophilizates for reconstitution with sterile water or a salt solution, preferably a saline solution. By introducing the polypeptides and immunogenic compositions into mammals, their immune systems are activated to produce antibodies against the polypeptide. Such antibodies, which are also a part of this invention, recognize the natural equivalent of the polypeptide in the malaria parasite and can therefore be used for passive immunization or for diagnostic purposes.

Antibodies against the polypeptides can be produced in monkeys, rabbits, horses, goats, guinea pigs, rats, mice, cows, sheep etc., and also in human beings. The antiserum or the purified antibodies can be used as required. The antibodies can be purified in a known manner e.g., by precipitation with ammonium sulphate. It is also possible to produce monoclonal antibodies which are directed against the polypeptides of the present invention using the method developed by Köhler et al. (Nature, 256, 495–497 [1975]). Polyclonal or monoclonal antibodies can also be used for the affinity-chromatographic purification of the polypeptides or their natural equivalents.

The polypeptides and immunogenic compositions of this invention can be used for the immunization of mammals against malaria. The mode of administration, the dosage and the number of injections can be optimized in a manner known to the person skilled in the art. Typically, several injections are administered over a long time period to obtain a high titre of antibodies against the malaria antigen.

EXAMPLE

The following abbreviations will be used throughout this example:

| | |
|---|---|
| ATP | adenosine triphosphate |
| bp | base pair |
| BSA | bovine serum albumin |
| cpm | impulse per minute |
| dATP | desoxyadenosine triphosphate |

| | -continued |
|---|---|
| dCTP | desoxycytidine triphosphate |
| dGTP | desoxyguanosine triphosphate |
| dTTP | desoxythymidine triphosphate |
| DTT | dithiothreitol |
| EDTA | ethylendiaminetetraacetic acid |
| IPTG | isopropyl β-D-thiogalactopyranoside |
| kb | 1,000 base pairs |
| kD | kilodalton |
| M | molar |
| mM | millimolar |
| ml | milliliter |
| nm | nanometer |
| PFU | plaque-forming units |
| RPM | revolutions per minute |
| SDS | sodium dodecylsulphate |
| TEMED | N,N,N',N'-tetramethylethylenediamine |
| Tris | trishydroxymethane |
| X-Gal | 5-bromo-4-chloro-3-indonyl β-D-galactopyranoside |

BUFFERS AND MEDIA

100×Denhardt's (100 ml)

2 g polyvinylpyrrolidone
2 g Ficoll
2 g BSA
100 mg sodium azide

DNA Gel Loading Buffer

1×TBE (see below for composition)
20% glycerol
0.1% bromophenol blue
0.1% xylenecyanol

Formamide Mix

80% (w/v) formamide
50 mM Tris/boric acid [pH 8.3]
1 mM EDTA
0.1% xylenexyanol
0.1% bromophenol blue

HIN Buffer 10 mM Tris/HCl [pH 7.4]
10 mM magnesium chloride
50 mM sodium chloride

Ligase Buffer 50 mM Tris/HCl [pH 7.8]
10 mM magnesium chloride
20 mM DTT
10 mM dATP

LB Medium: Per Liter 10 g Bactotrypton
5 g yeast extract
10 g sodium chloride

SDS Gel Loading Buffer

5% SDS
5 mM Tris/HCl [pH 6.8]
200 mM DTT
20% glycerol
0.1% bromophenol blue

20×SSC: Per Liter 175.3 g sodium chloride
82.2 g sodium citrate [pH 7.0]

SM Buffer 10 mM sodium chloride
10 mM magnesium chloride
10 mM Tris/HCl [pH 7.4]

10×T4 Polymerase Buffer 0.33M Tris/acetate [pH 7.9]
0.66M potassium acetate
0.10M magnesium acetate
5 mM DTT
1 mg/ml BSA

10×TBE 0.89M Tris/boric acid [pH 8.0]
0.89M boric acid
20 mM EDTA

10×TBS 0.5M Tris/HCl [pH 7.4]
1.5M sodium chloride

100×TE

1M Tris/HCl [pH 8.0]
100 mM EDTA

The following Methods were used several times in the following Example and are accordingly grouped together here.

Method 1: DNA Precipitation with Lithium Acetate

The DNA solution is treated with a tenth by volume of 5M lithium acetate and two volumes of isopropanol, mixed well and placed on dry ice for 10 minutes. The precipitated DNA is centrifuged for 10 minutes at 12,000 RPM (20° C.) in an Eppendorf bench centrifuge and the supernatant is carefully removed. The sediment is washed once with 80% (v/v) ethanol and subsequently dried for 5 minutes in a vacuum centrifuge. The DNA is dissolved in water and processed further.

Method 2: Agarose Gel Electrophoresis of DNA

The dried DNA is dissolved in 1×DNA gel loading buffer and heated to 65° C. for 5 minutes. 100 ml of 1×TBE buffer are mixed with agarose (800 mg for a 0.8% gel or 1.2 g for a 1.2% gel) and boiled until the agarose has dissolved completely. After cooling 2 μl of ethidium bromide solution (10 mg/ml) are added and the gel solution is poured into a horizontal gel electrophoresis apparatus (IBI, Genofit, Geneva, Switzerland). After solidification of the gel the samples are applied to the gel and the DNA is separated for 2 hours at 150 volt constant voltage. Commercial standard mixtures of DNA fragments of defined length (Gibco-BRL, Basle, Switzerland) are used as size markers. The DNA bands are visualized under 300 nm UV light.

Method 3: Isolation of DNA From an Agarose Gel

The DNA is separated on an agarose gel (Method 2). A piece of NA 45 nitrocellulose membrane (Schleicher and Schuell, Dassel, BRD) is placed in front of the bands which are to be isolated and the DNA is electrophoresed on to the membrane for 5 minutes at 200 V. The membrane is removed with forceps and washed under running, distilled water. The membrane is transferred into an Eppendorf test tube and the DNA is eluted at 65° C. for 10 minutes with 200 μl of 1.5M lithium acetate, 10 mM Tris/HCl [pH 8.0], 0.1 mM EDTA. The elution is repeated again. The combined supernatants are treated with 2 volumes of isopropanol. The precipitated DNA (Method 1) is dissolved in 50 μl of water.

Method 4: Plaque Purification of Lambda Phages

A bacterial culture (e.g. *E. coli* Y1088) is infected on an agar plate with lambda phages. Thereby, lytic plaques are formed in the lawn of bacteria. An agar cylinder (diameter 5 mm) containing a plague is cut from the agar with a inverted pasteur pipette. The agar cylinder is transferred into an Eppendorf test tube containing 500 μl of SM buffer and the test tube is shaken for 5 minutes.

The phage suspension is centrifuged (5 minutes at 12,000 RPM, 20° C.) and the supernatant is transferred into a fresh test tube. 1 μl of the phage suspension is diluted with 1 ml of SM buffer. 1, 10 and 100 μl of this solution are added to 50 μl of a cell suspension, $Mg^{++}$-treated in accordance with Morrison, Methods Enzymol, 68, 326-331 [1979]), of *E. coli* Y1090 containing the plasmid pMC9 (ATCC No. 37197).

After incubation at room temperature for 30 minutes, the solution is added to 3 ml of 0.8% (w/v) agar in LB medium and the mixture is poured on to LB-ampicillin agar plates (LB medium, 40 μg/ml ampicillin). Depending on the titre, some plates (e.g. those with the 1:1000 dilution) have individual plaques which, when they are positive in the antibody reaction or the DNA hybridization, can be isolated. The phages from the plaques can be grown up and used e.g., for the isolation of phage DNA.

Method 5: Isolation of Lambda Phage DNA

An individual plaque is picked from an agar plate with a sterile toothpick and the toothpick is incubated at 37° C. for 30 minutes in 500 μl of SM buffer. The toothpick is removed and the phage solution is centrifuged (10 minutes at 12,000 RPM, 20° C.). The supernatant is transferred into a fresh vessel and treated with 50 μl of chloroform. 100 μl of the phage solution are removed and mixed with 50 μl of a $Mg^{++}$-treated cell suspension of *E. coli* Y1090 cells (ATCC No. 37197).

After incubation at room temperature for 30 minutes the suspension is mixed with 3 ml of 0.8% (w/v) agar in LB medium and poured onto LB-ampicillin agar plates (see Method 4). After incubation at 37° C. for five hours, the Petri dishes are covered with 5 ml of SM buffer and shaken at room temperature overnight. Thereby, the phages are eluted from the agar.

The SM buffer containing the phages is poured off and centrifuged for 10 minutes at 12,000 RPM (room temperature). The supernatant (phage stock) is treated with 100 μl of chloroform. The phage titre in the phage stock usually amounts to $10^{10}$–$10^{11}$ PFU/ml. 50 ml of LB medium (containing 40 μg/ml of ampicillin and 10 mM magnesium chloride) are inoculated with 250 μl of a saturated culture of *E. coli* Y1088 containing plasmid pMC9 (ATCC No. 37195) and 1 ml of phage stock. The culture is shaken at 37° C. overnight.

After the addition of 2 ml of chloroform cell fragments are centrifuged off (10 minutes at 12,000 RPM, 20° C.). In each case 50 μl of a DNase I and RNase solution (in each case 10 mg/ml in water) are pipetted into the supernatant and the mixture is incubated at 37° C. for 30 minutes. 14 ml of 35% (w/v) polyethylene qlycol 6000 (SIGMA, St. Louis, Miss., USA), 2.5M sodium chloride are pipetted into the phage suspension (45 ml) and, after mixing well, the solution is placed on ice for one hour.

The phages are separated by centrifugation (20 minutes at 12,000 RPM, 4° C.) and dissolved in 1 ml of SM buffer. After the addition of 10 μl of 25% (w/v) lithium dodecylsulphate solution (Serva, Chemie Brunschwig AG, Basle, Switzerland) and 5 μl of 0.5M EDTA [pH 8.0]and a spatula tip of proteinase K (Merck, Darmstadt, BRD) the phage particles are lyzed at 65° C. for 10 minutes. 1 volume of phenol, which has previously been saturated with 1M Tris/HCl [pH 8.0], is added to the lysate. After mixing well the phases are separated by centrifugation (5 minutes at 6000 RPM). The supernatant is removed, the extraction is repeated and the DNA is precipitated from the second supernatant according to Method 1.

Method 6: Vector Preparation

1 μg of plasmid or phage DNA is digested at 37° C. for 1 hour with 10 units of restriction enzyme in 100 μl of T4 polymerase buffer. 400 μl of water and 5 units of bacterial phosphatase (Gibco-BRL) are pipetted in and the DNA is dephosphorylated at 65° C. for one hour. The solution is extracted twice with phenol and precipitated (Method 1). The vector fragment is purified via an agarose gel (Method 2), isolated (Method 3) and dissolved in 50 μl of water.

Method 7: Transformation of *E. coli*

A 3 ml LB culture is inoculated with *E. coli* cells and shaken at 37° C. overnight. 1 ml of this saturated culture is used to inoculate a 50 ml LB liquid culture. This is shaken until the optical density at 600 nm ($OD_{600}$) has reached a value of 0.2. The cells are sedimented (5 minutes at 6000 RPM, room temperature) and resuspended in 50 ml of ice-cold 50 mM calcium chloride. The solution is placed on ice for 30 minutes. The cells are again centrifuged off (see above) and suspended in 10 ml of 50 mM calcium chloride 20% glycerol. The competent cells are frozen at −80° C. in 500 μl portions.

For the transformation, a portion is thawed slowly on ice (30 minutes). 10 μl of DNA solution (1–10 ng), 8 μl of 30% (w/v) polyethylene glycol (SIGMA), 10 μl of 500 mM magnesium chloride 100 mM calcium chloride and 72 μl of water are mixed well and incubated with 100 μl of competent cells for 20 minutes on ice. Subsequently, the mixture is incubated at room temperature for a further 10 minutes.

When using vectors of the M13 type (Yanisch-Perron et al., Gene 33, 103–119 [1985]), there are now added 50 μl of 10% (w/v) x-Gal (Gibco-BRL) in dimethylformamide 10 μl of 100 mM IPTG (Gibco-BRL) in water and 50 μl of a saturated TG-1 (Amersham, Braunschweig, BRD) culture. After mixing well 3 ml of 0.8% (w/v) agar in LB medium are added and the mixture is poured on to a LB agar plate. The Petri dishes are incubated at 37° C. overnight.

When using plasmid DNA, which can be selected for antibiotic resistance (pUC, pDS78/RBSII, 6xHis, etc.), 1 ml of LB medium is added to the transformation mixture and the incubation is carried out at 37° C. for one hour. The cells are centrifuged off for 3 minutes at 6,000 RPM (room temperature) and resuspended in 100 μl of LB medium. These 100 μl are distributed uniformly by means of a rotating disc (Schütt, Göttingen, BRD) on a LB agar plate which contains the antibiotic required for the selection and likewise incubated at 37° C. overnight.

Method 8: Preparation of the DNA for Sequencing

When TG-1 bacteria having a vector of the M13 type which contains a DNA fragment to be sequenced are transformed as described above, white plaques result. These white plaques are picked with a toothpick and resuspended in 3 ml of LB medium. Thereto there are added a further 10 $\mu$l of a saturated TG-1 culture. The mixture is shaken at 37° C. for 5 hours. 1.5 ml of culture are transferred into an Eppendorf test tube and centrifuged (5 minutes at 12,000 RPM 20° C.), 800 $\mu$l of supernatant are transferred into a new test tube and mixed with 200 $\mu$l of 20% (w/v) polyethylene glycol, 2.5M sodium chloride solution and incubated at room temperature for 20 minutes. The remainder of the culture is stored at 4° C. or used for the preparation of "mini-lysate" DNA (Method 10).

The phages are precipitated by centrifugation (10 minutes at 12,000 RPM, 20° C.). The sediment is dissolved in 100 $\mu$l of 1×TE buffer and extracted with 100 $\mu$l of saturated phenol. The phases are separated by centrifugation (5 minutes at 12,000 RPM). 80 $\mu$l of the aqueous phase are transferred into a new reagent test tube, the DNA is precipitated and dissolved in 12 $\mu$l of water (Method 1).

Method 9: DNA Sequencing According to Sanger

3 $\mu$l of the DNA prepared according to Method 8 are mixed with 2 $\mu$l of water. 1 $\mu$l of HIN buffer, 1 $\mu$l of 25 $\mu$M dATP, 2 $\mu$l of alpha-[$^{32}$P]-ATP (6000 Ci/mmol, Amersham) and 1 $\mu$l of sequencing starter (Pharmacia, Dübendorf, Switzerland) and heated at 55° C. for 5 minutes. Thereafter, the solution is placed on ice. In the meantime, 4 test tubes each containing 3 $\mu$l of the stop solutions A$^o$, G$^o$, T$^o$ and C$^o$ are prepared. The stop solutions have the following composition: A$^o$: 3 $\mu$M ddATP, 112 $\mu$M dCTP, 112 $\mu$M dGTP, 112 $\mu$M dTTP C$^o$: 100 $\mu$M ddCTP, 11.5 $\mu$M dCTP, 112 $\mu$M dGTP 112 $\mu$M dTTP G$^o$: 100 $\mu$mM ddGTP, 112 $\mu$M dCTP, 5.6 $\mu$M dGTP, 112 $\mu$M dTTP T$^o$: 500 $\mu$M ddTTP, 85 $\mu$M dCTP, 85 $\mu$M dGTP, 5.6 $\mu$M dTTP.

5 units of Klenow polymerase (Pharmacia) are pipetted into the test tubes containing the DNA and mixed well. In each case 3 $\mu$l of this solution are mixed with the stop solution and incubated at 37° C. for 10 minutes. 1 $\mu$l of 0.25 mM dATP is added to each of the four test tubes, mixed and again incubated for 10 minutes. Finally, the reaction is stopped by adding 2 $\mu$l of formamide mix and heating to 96° C. for 5 minutes. The DNA is now applied to a 0.2 mm gel of the following composition:

6 ml 10×TBE-buffer
28.8 g urea
3.6 g acrylamide (Bio-Rad Laboratories AG, Glattbrugg, Switzerland)
180 mg bisacrylamide (Bio-Rad)
400 $\mu$l 10% ammonium persulphate
20 $\mu$l TEMED The DNA is separated electrophoretically for 1 to 6 hours at 40 watts constant output. The glass plates are separated and the gel is fixed for 5 minutes in 10% (v/v) acetic acid and 10% (v/v) methanol. The gel is then washed twice with 10% (v/v) methanol for 5 minutes, mounted on Whatman 3MM paper (Bender and Hobein, Zurich, Switzerland) and dried in a gel dryer. The dried gel is autoradiographed for 2 to 20 hours with KODAK-XAR film (Eastman Kodak Co., Rochester, N.Y., USA).

Method 10: DNA Isolation on a Small Scale ("mini-lysate")

About 1 to 2 ml of bacterial culture (e.g., *E. coli* TG-1 containing a vector of the M13 type; see Method 8) are centrifuged for 5 minutes at 12,000 RPM (20° C.). The supernatant is carefully sucked off. The sedimented cells are resuspended in 500 $\mu$l of 50 mM Tris/HCl [pH 7.6], 5 mM EDTA. After the addition of a small spatula tip of lysozyme (SIGMA) the suspension is incubated at room temperature for 5 minutes. 15 $\mu$l of 25% (w/v) lithium dodecylsulphate solution (SIGMA) and 30 $\mu$l of 5M potassium acetate are then added and the suspension is mixed carefully. After incubation on ice for 15 minutes the sample is centrifuged for 15 minutes at 12,000 RPM (4° C.). The supernatant is decanted into a new test tube and treated with 50 $\mu$l of RNase solution (10 mg/ml). After incubation at 37° C. for 5 minutes, the sample is extracted once with phenol and once with chloroform (in each case the same volumes). The DNA in the aqueous phase is precipitated (Method 1) and finally dissolved in 100 $\mu$l of water.

Method 11: Radioactive Labelling of DNA ("nick translation")

The following reagents are pipetted into 20 $\mu$l of DNA solution:

5 $\mu$of HIN buffer, 10 $\mu$l of alpha-[$^{32}$P]-ATP (6000 Ci/mMol, Amersham), 5 $\mu$l of DNase I (1 ng/ml), 5 $\mu$l of 1 mM dCTP, dGTP, dTTP and 5 $\mu$l of DNA polymerase I (Boehringer Mannheim AG, Rotkreuz, Switzerland). The batch (50 $\mu$l) is incubated at 14° C. for 90 minutes and subsequently extracted once with phenol (see Method 5). The aqueous phase contains the DNA probe and is used directly for hybridization experiments.

Method 12: Hybridization of DNA

The filter containing DNA is incubated for one hour at 60° C. with pre-hybridization mix (2×SSC, 0.1% (w/v) lithium dodecylsulphate, 10 $\mu$g/ml of denatured calf thymus DNA, 5×Denhardt's, 5×TE buffer). The calf thymus DNA is previously denatured by boiling. The pre-hybridization mix is replaced by hybridization mix which corresponds to the pre-hybridization mix, but which additionally contains about 10$^7$ cpm of radioactive sample. After incubation at 60° C. overnight the filters are washed 3 times for 30 minutes in 2×SSC. The filters are dried and exposed overnight against Kodak XAR film.

Method 13: Preparation of a 12% SDS Polyacrylamide Gel According to Laemmli, Nature 227, 680–685 [1970]

| | |
|---|---|
| 60 ml separating gel | 15 ml 1.5.M Tris/HCl [pH 8.8], 0.4% (w/v) SDS, 8 mM EDTA. 24 ml 29% (w/v) acrylamide (Bio-Rad), 1% (w/v) bisacrylamide (Bio-Rad) in water 25 ml water. 500 $\mu$l 10% (w/v) ammonium persulphate in water. |

The solutions are mixed. Immediately before pouring between 2 glass plates 100 $\mu$l of TEMED are added. After the separating gel has polymerized the collecting gel having the following composition is poured in:

| | |
|---|---|
| 20 ml collecting gel: | 5 ml 0.5M Tris/HCl [pH 6.8], 0.4% (w/v) SDS, 8 mM EDTA. |
| | 3 ml 29% (w/v) acrylamide, 1% (w/v) bisacrylamide in water. |
| | 12 ml water. |
| | 250 μl 10% (w/v) ammonium persulphate solution in water. |

After mixing, 30 μl of TEMED are added and a probe comb is inserted prior to the polymerization. 190 mM glycine, 25 mM Tris [pH 7.6], 1% (w/v) SDS is used as the electrophoresis buffer. Commercial molecular weight standards (Bio-Rad) are applied as size markers.

Method 14: Immunoblots (Western blot)

4 μl of a protein sample are separated on a 12% SDS polyacrylamide gel for 45 minutes at 25 mA constant current. The gel is removed and placed in transfer buffer. A sheet of nitrocellulose (Schleicher & Schuell), moistened with water, is placed on the gel. Gel and nitrocellulose are covered with Whatman 3MM paper and then a sponge is placed on each of them. The sandwich which is thus obtained is then introduced into an electrophoresis apparatus, whereby the nitrocellulose is directed towards the positive pole. The transfer of the proteins is effected at 400 mA constant current for 15 minutes. After the transfer, the nitrocellulose is shaken for 10 minutes in 1×TBS buffer.

The nitrocellulose is pre-incubated for 30 minutes in 1×TBS, 5% (w/v) skimmed milk powder. The antibody against the parasite antigen is diluted in the ratio 1:1000 in 1×TBS, 5% (w/v) skimmed milk powder and incubated for one hour with the nitrocellulose sheet. Thereafter, the sheet is washed five times for three minutes in fresh 1×TBS and subsequently incubated for one hour with goat-anti-rabbit-peroxidase serum (Biorad; diluted 1:1000) in 1×TBS, 5% (w/v) skimmed milk powder. The nitrocellulose is again washed as above and subsequently placed in 5 ml of 1×TBS.

The solution is treated with 10 ml of a 4-chloronaphthol solution (SIGMA, 50 mg/ml in methanol) and mixed well. The colour reaction is started by the addition of 50 μl of hydrogen peroxide. After the bands have been made visible, the nitrocellulose sheet is stored in water to prevent an overexposure. Pre-stained marker proteins, which are used according to details of the manufacturer (e.g. Gibco-BRL), are employed as the molecular weight markers.

Method 15: Southern Transfer of DNA onto Nylon Membranes

About 10 μg of plasmid or parasite DNA per trace are separated on an agarose gel (Method 2). After elution the gel is photographed and agitated twice for 15 minutes in 0.2N HCl. Subsequently, the gel is agitated twice for 15 minutes in 0.5M sodium hydroxide solution. The gel is neutralized twice for 15 minutes in 0.5 M Tris/HCl [pH 8.0], 1.5M sodium chloride, and placed on a sponge which is soaked with 20×SSC. A nylon membrane (PALL, Basle, Switzerland) is placed on the gel, followed by 3 sheets of Whatman 3MM paper and about 20 paper towels. The assembly is weighed down from above with a 500 g weight. After 3 hours the membrane is removed and dried, firstly at room temperature and subsequently for 1 hour at 80° C. in a vacuum.

The membrane can be treated further in accordance with Method 12.

CONSTRUCTION OF THE PLASMID pDS78/RBSII,6xHis

1. Description of the Plasmids pDS78/RBSII and pDMI,1

The plasmid pDS78/RBSII was used for the construction of the plasmid pDS78/RBSII,6xHis. E. coli M15 cells transformed with this plasmid and with the plasmid pDMI,1 have been deposited at the Deutsche Sammlung von Microorganism in Göttingen on the 3rd September 1987 [E. coli M15 (pDS78/RBSII; pDMI,1), DSM No. 4232].

The part of pDS78/RBSII (FIG. 1 and 2), which lies between the restriction cleavage sites for XbaI and XhoI and the replication region as well as the gene for β-lactamase, which confers ampicillin resistance to the cells, stems originally from the plasmid pBR322 (Bolivar et al., Gene 2, 95–113 [1977]; Sutcliffe, Cold Spring Harbor Symp. Quant. Biol. 43, 77–90 [1979]). However, the gene for the β-lactamase is modified by elimination of the cleavage sites for the restriction enzymes HincII and PstI. These alterations in the DNA sequence do not, however, affect the amino acid sequence of the β-lactamase. The remaining part of the plasmid carries the regulatable promoter/operator element N25OPSN25OP29 (R. Gentz, Thesis, University of Heidelberg, BRD [1984]) and the ribosomal binding site RBSII. This ribosomal binding site was derived from the ribosomal binding site of the promoter $P_{G25}$ of the E. coli phage T5 (R. Gentz, supra) and is obtained as the EcoRI/BamHI fragment by DNA synthesis. There follows the dihydrofolate reductase gene of the mouse cell line AT-3000 (Chang et al., Nature 275, 617–624 [1978]; Masters et al., Gene 21, 59–63 [1983]) which has been altered by introducing a cleavage site for the restriction enzyme BglII directly in front of the termination codon for translation. Furthermore, the plasmid pDS78/RBSII contains the terminator $t_o$ of the E. coli phage lambda (Schwarz et al. Nature 272, 410–414 [1978]), the promoter-free gene of chloramphenicol acetyltransferase (Marcoli et al., FEBS Letters, 110, 11–14 [1980]) and the terminator T1 of the E. coli rrnB operon (Brosius et al., J. Mol. Biol., 148, 107–127 [1981]).

pDS78/RBSII contains the regulatable promoter/operator element N25OPSN25OP29 and the ribosomal binding site RBSII. Because of the high efficiency of this expression signal, the plasmid pDS78/RBSII and its derivatives such as the plasmid pDS78/RBSII,6xHis can be stably maintained in E. coli cells only when the promoter/operator element is repressed by the bonding of a lac repressor to the operator. The lac repressor is coded by the lacI gene. N25OPSN25OP29 can be repressed efficiently only when a sufficient number of repressor molecules is present in the cells. Therefore, the lacI $q$ allele, which contains a promoter mutant leading to an increased expression of the repressor gene, was used. This lacI$q$ allele is contained in the plasmid pDMI,1 (FIG. 3 and 4).

This plasmid carries, in addition to the lacI gene, the neo gene which confers kanamycin resistance to the bacteria. Kanamycin resistance can be used as the selection marker. pDMI,1 is compatible with the above-mentioned plasmids. E. coli cells which are transformed with the expression vectors described above must contain pDMI.1 to guarantee that the expression vector is held stable in the cells. An induction of this system is achieved by adding IPTG to the medium at the desired cell density.

The plasmid pDMI,1 (FIG. 3 and 4) carries the neo gene of neomycin phosphotransferase from the transposon Tn5 (Beck et al., Gene 19, 327–336 [1982]), which confers kanamycin resistance to the E. coli cells, and the lacI gene (Farabough, Nature 274, 765–769 [1978]) with the promoter mutation I$^q$ (Calos, Nature 274, 762–765 [1978]), which codes for the lac repressor. Moreover, the plasmid pDMI,1 contains a region of the plasmid pACYC184 (Chang et al., J. Bacteriol. 134, 114–1156 [1978]), which contains all information required for the replication and stable transmission to the daughter cells.

2. Construction of the Plasmid pDS78/RBSII,6xHis

For the construction of the plasmid pDS78/RBSII,6xHis (FIG. 5 and 6), the EcoRI/BamHI fragment of pDS78/RBSII comprising the ribosomal binding site RBSII was supplemented with a region coding for six histidines.

For this purpose, two complimentary oligonucleotides, the nucleotide sequences of which are represented in FIG. 5 as a double-stranded DNA sequence, were first produced simultaneously on a multisynthesis apparatus (described in European Patent Application, Publication No. 181 491, published on the 21.05.85), with controlled pore glass (CPG) being used as the carrier material (Kiefer et al., Immunol. Meth. 3, 69–83 [1985]; Sproat et al., Tetrahedr. Lett., 24 5771–5774 [1983]; Adams et al., J. Amer. Chem. Soc., 105, 661–663 [1985]). The lyophilized oligonucleotides were taken up in water and dissolved at 4° C. for 1 hour. The DNA concentration amounted to 100 nMoles/ml. For the phosphorylation, in each case 150 pMoles of the two oligonucleotides in 20 μl of 50 mM Tris/HCl [pH 8.5] and 10 mM MgCl$_2$ were incubated at 37° C. for 20 minutes with 2 pMoles of γ-[$^{32}$P]-ATP (5,000 Ci/mMole, Amersham,) and 1 unit (U) of T4-polynucleotide kinase (Gibco-BRL). Subsequently, 5 nMoles of ATP were added and, after a further 20 minutes at 37° C., the reactions were terminated by heating to 65° C.

The DNA of the plasmid pDS78/RBSII was prepared for ligation with the two phosphorylated oligonucleotides by first cleaving 2 pMoles of the plasmid DNA with the restriction enzyme BamHI, following the manufacturer's instructions. The DNA was extracted with phenol washed with ether and precipitated as described in Method 1. The sediment was dried and taken up in 20 μl of TE buffer.

For the ligation with the phosphorylated oligonucleotides, 1.5 pMoles of the plasmid DNA cleaved with BamHI were incubated at 15° C. for 2 hours with in each case 60 pMoles of the phosphorylated oligonucleotides in ligase buffer containing 2 units of T4-DNA ligase. After a further incubation at 65° C. for 5 minutes, the ligated DNA was cleaved with the restriction enzymes XhoI and BamHI according to details of the manufacturers, before the XhoI/BamHI fragment F comprising the regulatable promoter N25OPSN-25OP29, the ribosomal binding site RBSII and the region coding for 6 histidines (FIG. 5) was isolated using Method 3.

For the construction of the plasmid pDS78/RBSII,6xHis, the XhoI/BamHI fragment F described above was integrated into the plasmid pDS78/RBSII, whereby the original XhoI/BamHI fragment of this plasmid was replaced (FIG. 6). For this purpose, 1 pMole of DNA of the plasmid pDS78/RBSII was first cleaved with the restriction enzymes XhoI and BamHI, and the larger DNA fragment was isolated using Method 3. 0.05 pMoles of this fragment were incubated at 15° C. for 2 hours with 0.1 pMoles of the isolated XhoI/BamHI fragment F in ligation buffer with 2 units of T4-DNA ligase. E. coli M15 cells transformed with plasmid pDMI,1 were prepared for the transformation with pDS78/RBSII,6xHis according to the method of Morrison (Methods Enzymol. 68, 326–331 [1979]).

After heating to 65° C. for 7 minutes, the ligation mixture was added to 200 μl of these competent cells. The sample was held in ice for 30 minutes, then incubated at 42° C. for 2 minutes and, after the addition of 0.5 ml of LB medium, incubated at 37° C. for 90 minutes. The cells were plated out on LB agar plates which contained 100 μg/ml of ampicillin and 25 μl ml of kanamycin and incubated at 37° C. overnight in an incubator.

Individual colonies were picked with a sterile toothpick and incubated in 10 ml of LB medium containing 100 μl/ml ampicillin and 25 μg/ml kanamycin for 12 hours in a shaking incubator. Thereafter the cells were sedimented and the plasmid DNA was isolated according to the method of Birnboim et al. (Nucleic Acids Res. 7, 1515–1523 [1979]).

In each case 0.2 μg of the isolated plasmids were cleaved with the restriction enzymes XhoI and BamHI, to examine whether the XhoI/BamHI fragment F was present in these plasmids. Plasmids having such a fragment received the designation pDS78/RBSII,6xHis (FIG. 6).

To demonstrate that the correct sequence was present in pDS78/RBSII,6xHis, the double-stranded circular plasmid DNA was sequenced, with a γ-[$^{32}$P]-ATP labelled starter sequence ("primer") being used. This starter sequence contained the nucleotides of position 89–108 of the plasmid pDS78/RBSII. 0.3 pMoles of the isolated plasmid DNA were precipitated with alcohol, and the sediment was washed once with 80% (v/v) ethanol, dried and dissolved in 8 μl of ¼ TE buffer.

The sample was incubated at 95° C. for 5 minutes, cooled to 0° C. and centrifuged (2 minutes, 12,000 RPM). 1.5 pMoles of the starter sequence in a volume of 2 μl were added before the sample was incubated at 95° C. for 2 minutes and then at 42° C. for 5 minutes. The DNA was then sequenced according to the method of Sanger et al. (Proc. Natl. Acad. Sci. USA 74, 5463–6567 [1977]. Because a radioactively labelled "primer" was used, all reactions were carried out with unlabelled deoxynucleotide triphosphates. The DNA sequence analysis indicated that pDS78/RBSII,6xHis contained the sequence given in FIG. 5.

Isolation of a P. falciparum gene with antibodies from a genomic expression gene bank

Construction of the expression gene bank of P. falciparum

P. falciparum cells (KI isolate) were grown by usual methods (Trager et al., Science 193, 673–675 [1976]) in 10 culture dishes and subsequently washed in culture medium containing 0.1% saponin. The washed parasites were resuspended in 2 ml of 10 mM EDTA, pH 8.0, 0.5% (w/v) SDS. After the addition of 50 mg of proteinase K (Merck), the mixture was incubated at 65° C. for 10 minutes and then treated with 2 ml of phenol (saturated with Tris/HCl [pH 8.0]). The phases were mixed by shaking and again separated by centrifugation (10 minutes at 6,000 RPM, 20° C.). The phenol extraction was repeated twice (an interphase should no longer be visible).

The DNA was precipitated according to Method 1, washed with ethanol, dried and then dissolved in 2 ml of water and cut mechanically, i.e. squeezed 80 times through a syringe having a 0.5×16 mm needle. Thereafter, 0.2 volumes of 5×EcoRI methylase buffer (50 mM Tris/HCl [pH 7.5], 0.25M NaCl, 50 mM EDTA, 25 mM β-mercaptoethanol, 0.4 mM S-adenosylmethionine) were added. 10 μg of DNA were methylated at 37° C. for 30 minutes with 50 units of EcoRI methylase (New England Biolabs, Beverly, Mass., USA).

The DNA was extracted once with phenol as described above and precipitated in accordance with Method 1. The DNA was dissolved in 200 μl of T4 polymerase buffer and, after the addition of 5 μl of 5 mM dATP, dCTP, dGTP and dTTP and 10 units of T4 polymerase (Gibco-BRL), incubated at 37° C. for 30 minutes. The DNA was again extracted with phenol and precipitated in accordance with Method 1.

The DNA was dissolved in 50 μl of T4-DNA ligase buffer and, after the addition of 0.01 $OD_{260}$-units of phosphorylated EcoRI oligonucleotide adaptors (New England Biolabs) and 2 μl of T4-DNA ligase (12 Weiss units, New England Biolabs), ligated at 14° C. overnight. The DNA was precipitated according to Method 1, dissolved in 20 μl of 1×DNA gel loading buffer and separated on a 0.8% agarose gel (Method 2). DNA fragments having a length of 2 to 6 kb (1 kb=1,000 nucleotides) were isolated in accordance with Method 3.

The DNA obtained was dissolved in 50 μl of water and, after the addition of 6 μl of 10×ligase buffer, 2 μl of dephosphorylated lambda arms (Promega Biotech., Madison, Wis.) and 6 Weiss units of T4-DNA ligase, ligated at 14° C. overnight. The DNA was precipitated (Method 1) and dissolved in 5 μl of water. After the addition of 20 μl of "Packaging Extract" (Genofit, S.A., Geneva, Switzerland), the DNA was packed in phage particles at 20° C. for 2 hours according to the directions of the manufacturer. After the addition of 500 μl of SM buffer and 50 μl of chloroform, the gene bank was ready for the antibody test.

Antibody Test of the Gene Bank

Antibodies against surface proteins of the merozoite stage of *P. falciparum* were produced in rabbits as described by Perrin et al. (J. Clin. Invest. 75, 1718–1721 [1984]). An antiserum which was specific for a *P. falciparum* K12 merozoite surface antigen having a molecular weight of 41,000 was selected for the antibody test of the gene bank.

*E. coli* Y1090 in 3 ml of LB medium containing 40 μl/ml of ampicillin was incubated at 37° C. overnight in a shaking bath. On the next morning the cells were sedimented (10 minutes at 7,000×g, 20° C.) and resuspended in 1 ml of SM buffer. $10^6$ infectious phage particles of the gene bank were added to this cell suspension and incubation was carried out at room temperature for 30 minutes. 60 ml of 0.8% agar solution in LB medium, warmed to 42° C., were added and mixed well. The soft agar containing the infected cells was distributed on 6 LB agar plates (diameter 135 mm) containing 40 μg/ml ampicillin and incubated at 42° C. for 5 hours A nitrocellulose filter (Schleicher and Schuell), immersed in 100 mM IPTG solution and dried, was placed on each dish and incubation was carried out at 37° C. overnight. On the next day the position of the filter relative to the dish was marked and the marked filter was stored in 1×TBS. A new nitrocellulose filter, treated in 100 mM IPTG solution, was placed on the plate, marked and incubated at 37° C. for 4 hours on the plate. The two filter batches were shaken for 10 minutes in 1×TBS, then incubated for 20 minutes in 1×TBS, 20% FCS (foetal calf serum).

The rabbit antiserum was diluted 1:1000 with 1×TBS/20% FCS, and the two filter batches were incubated at room temperature for one hour in a shaking bath. The filters were washed three times for three minutes in 1×TBS, 0.1% Triton TM -X-100 (Bio-Rad) in a shaking bath, followed by an incubation for one hour with 5 μCi of [$^{125}$I]-protein A (Amersham Catalogue No. 1M.144) in 1×TBS, 0.1% protease-free bovine serum albumin (SIGMA). The filters were again washed as above and the filters were dried at room temperature.

The filters were exposed overnight against Kodak XAR. Plaques which were present on both plates were identified with the aid of the markings and picked from the Petri dishes on the basis of the marking. The individual samples were again plated out in soft agar in different dilutions according to Method 4, and positive plaques were again identified as described above. An individual, positive plaque (Kl-A) was picked, the lambda phages were grown up according to Method 5 and the DNA was isolated.

10 μg of Kl-A DNA were dissolved with 490 μl of T4 polymerase buffer and digested at 37° C. for one hour with 50 units of HindIII. The DNA was precipitated (Method 1) and analyzed on a 0.8% agarose gel (Method 2). 10 μg of gt11 DNA were digested with HindIII and analyzed as the control. A HindIII fragment (270 base pairs) was now present in the trace having the Kl-A DNA. The fragment was isolated (Method 3), dissolved in 50 μl of water and stored at 4° C.

For sequencing, 50 ng of HindIII-cleaved, dephosphorylated M13 mp18 DNA (Pharmacia; Method 6) were mixed with 10 μl of the dissolved HindIII fragment from Kl-A, 2 μl of 10×ligase buffer, 6 μl of water and 6 Weiss units of T4-DNA ligase (New England Biolabs) were added, and the DNA's were ligated at room temperature for one hour. Competent TG-1 *E. coli* cells were transformed with the ligated DNA (Method 7). A white plaque was isolated, amplified and sufficient DNA for the sequence determination was isolated (Method 8). The DNA sequence was determined according to Method 9. An M13 mp18 clone having the HindIII fragment was denoted as Kl-A-M.

The HindIII fragment from the Kl-A-M DNA was used to isolate a longer piece of DNA which coded for the merozoite antigen. For this purpose, the double-stranded DNA of the M13 clone Kl-A-M was isolated (Method 10). After the addition of 20 units of HindIII, 5 μg of DNA were digested at 37° C. for one hour. The solution was again precipitated (Method 1). The DNA was separated on a 1.2% agarose gel (Method 2). The 270 bp HindIII fragment was isolated (Method 3) and the purified DNA was dissolved in 20 μl of water. The DNA was labelled by "nick translation" (Method 11).

The *P. falciparum* lambda gene bank was again plated as described above (2×10 phage particles on two Petri dishes of 135 mm diameter). After five hours, as plaques became visible, the Petri dishes were removed from the 37° C. incubator and stored overnight in a refrigerator. PALL nylon filters (PALL, Basle, Switzerland) were placed on the cold dishes and the relative positions of the filters to the Petri dishes were marked with ink.

After 5 minutes the filters were withdrawn carefully from the plates and placed with the side having the plaques upwards on Whatman 3MM paper which had previously been soaked with alkaline solution (0.5M sodium hydroxide and 0.5M Tris). After a few minutes, the filters were placed on a new Whatman 3MM paper soaked with the alkaline solution. Thereafter, the filters were dried briefly on a 3MM filter paper and then placed twice for five minutes on Whatman 3MM paper which had previously been soaked with 1.5M NaCl, 0.5M Tris/HCl [pH 8.0]. The filters were then dried in air and baked at 80° C. for 90 minutes in a vacuum. The hybridization of the filters with the 270 bp HindIII fragment ($1 \times 10^7$ cpm) as the probe was carried out according to Method 12.

Positive plaques were picked as described above, and the specificity of the hybridization was examined with the radioactive probe according to Methods 4 and 12. An individual plaque, Kl-B, was grown up according to Method 5 and the DNA was digested with HindIII as described above and separated on agarose gels (Method 2). The HindIII fragments, which were not present in the vector DNA, were isolated, cloned in M13 mp18 and sequenced (Methods 6, 7, 8 and 9).

Restriction Analysis of the *P. falciparum* DNA in the Kl-B DNA

1 μg of Kl-B lambda DNA in 50 μl of T4 polymerase buffer was digested with 5 units of EcoRI for one hour. The DNA was analyzed (Method 2) and a 1.3 kb fragment was isolated (Method 3). The isolated fragment DNA was dissolved in 20 μl of water. 1 μg of pUC18 DNA (Pharmacia) was digested with 5 units of EcoRI and processed further according to Method 6. After isolation from the gel (Method 3) the linearized vector was dissolved in 50 μl of water. 1 μl of vector were incubated at room temperature for 1 hour with 5 μl of 1.3 kb fragment. 1 μl of 10×ligase buffer and 6 Weiss units of T4-DNA ligase.

E. coli cells were transformed with the DNA in accordance with Method 7, and the plasmid DNA was isolated from the transformants (Method 10). The plasmid obtained was designated as PKl-B. In each case 0.5 μg of PKl-B DNA were digested as described above with the restriction enzymes SphI, XmnI, HPaI and, in double digestions additionally with HindIII and analyzed on an agarose gel according to Method 2. The entire sequence of the *P. falciparum* DNA in pKl-B could be determined with the aid of this restriction analysis.

Expression of the HPaI/SphI Fragment in *E. coli*

A HpaI/SPhI fragment specific for *P. falciparum* was isolated from the clone pKl-B in accordance with Methods 1 to 3. 6 μg of PKl-B DNA were digested at 37° C. for one hour with 15 units of HPaI and 15 units of SPhI in 100 μl of 1×T4 polymerase buffer. The DNA was precipitated (Method 1) and separated on a 0.8% agarose gel (Method 2), and a 700 bp fragment was isolated (Method 3). The fragment was resuspended in 20 μl of water and, after the addition of 10 pMoles of a phosphorylated BamHI oligonucleotide adaptor (12-mer: CCCGGATCCGGG; New England Biolabs), 2.5 μl of 10×ligase buffer and 6 Weiss units of T4 DNA ligase. ligated at 14° C. overnight. The DNA was precipitated (Method 1), dissolved in 50 μl of 1×T4 polymerase buffer and, after the addition of 40 units of BamHI, digested at 37° C. for 1 hour. The DNA was precipitated (Method 1) and separated on a 1.0 percentage agarose gel (Method 2). A 700 bp fragment was isolated (Method 3) and dissolved in 10 μl of water. For the preparation of the vector (see Method 6), 1 μg of pDS78/RBSII,6xHis vector DNA was digested at 37° C. with 10 units of BamHI for one hour in T4 polymerase buffer. The vector DNA was dephosphorylated (Method 4), extracted once with phenol (see above), purified on a 0.8% agarose gel (Method 2) and subsequently isolated according to Method 3. The isolated DNA was dissolved in 50 μl of water.

5 μl of the linearized pDS78/RBSII,6xHis vector DNA, which had been digested with BamHI and dephosphorylated (Method 6), were incubated at room temperature for one hour with 5 μl of the 700 bp fragment, 1.2 μl of 10×ligase buffer and 6 Weiss units of T4-DNA ligase. 10 μl of DNA were then transformed into competent M15 (pDMI,1) cells (Method 7) and plated on LB plates with 100 μg/ml ampicillin and 25 μg/ml kanamycin. Individual colonies were picked with a toothpick and transferred into 3 ml of LB medium containing 100 μg/ml ampicillin and 25 μg/ml kanamycin. The cultures were incubated at 37° C. in a shaking water bath until the optical density at 600 nm ($OD_{600}$) increased to 0.6 compared with pure medium.

An aliquot of 500 μl of the culture was removed as a non-induced control. IPTG (1 mM final concentration) was added to the remainder of the culture and the induced culture was incubated for a further 3 hours. Thereafter, 500 μl of the induced culture were removed and centrifuged together with the non-induced sample (3 minutes at 12,000 RPM 20° C.). The supernatant was sucked off and the cell sediment was resuspended in 100 μl of SDS sample buffer.

The samples were boiled for 7 minutes and the proteins were separated on a 12% SDS gel (Method 13) by means of electrophoresis (three hours at 50 mA constant current). The gel was stained for 30 minutes on the shaker with 0.1% Coomassie blue in 30% (v/v) acetic acid and 10% (v/v) methanol. The gel was decolorized at 65° C. for 2 hours in 10% (v/v) methanol and 10% (v/v) acetic acid. Clones which, compared with the uninduced sample exhibited an additional band having the expected molecular weight of 27 kD were analyzed according to Method 14. The novel protein was denoted as protein (27 kD). The amino acid sequence of the expressed protein corresponded to amino acid sequence (II).

Analysis of 11 Different Parasite Isolates with Antibodies Against the Antigen

The following 11 isolates of *P. falciparum* were tested: RO-33, Ghana; RO-56. Ethiopia; Geneva No. 13. Senegal; H-B3, Honduras; RO-53, Cameroon; R-FCR 3, Gambia; MAD-20, Papua New Guinea; 542, Brazil; RO-58, East Africa; FCH-5-C2, Tanzania; Kl, Thailand. The parasites were isolated from malaria patients and cultivated according to standard methods. Malaria parasites from other isolates of *P. falciparum* can, however, also be used. Parasites from two culture dishes were centrifuged off (10 minutes at 1,500 RPM, 4° C.) and dissolved in 200 μl of SDS-gel loading buffer. After boiling for seven minutes the samples were separated on a SDS gel (Method 13). The samples were transferred to nitrocellulose and tested with antibodies against the antigen (Method 14). The result (FIG. 7) showed that the antigen was present in all isolates and had a similar molecular weight in all isolates.

Analysis of Parasite Isolates with Gene Probes from K1

The EcoRI fragment from PK1-B was isolated in accordance with Methods 2 and 3 and labelled by "nick translation" (Method 11). The labelled probe was used as the hybridization probe ($10^6$ cpm). In each case 10 µg of DNA were isolated (see above) from different *P. falciparum* isolates, digested with 50 units of DraI in T4 polymerase buffer and separated on a 1.2% agarose gel (Method 2). The DNA was transferred to a nylon filter (Method 15) and subsequently hybridized (Method 12). The result (FIG. 8) showed a uniform band pattern in the case of all tested isolates and proved together with sequence data of DNA from different isolates on the plane of the DNA that the antigen, which corresponds to the polypeptides of the invention, is preserved.

EXPRRESSION AND PURIFICATION OF PROTEIN (41 kD)

1. Construction of the Expression Vector

1 µl of PKI-B DNA (concentration 0.5 µg/µl ) was mixed with 100 µl of 1×T4 polymerase buffer. After the addition of 5 units of EcoRI the mixture was incubated at 37° C. for 1 hour. The sample was precipitated with isopropanol (Method 1) and separated on a 0.8% agarose gel (Method 2). The 1.3 kb EcoRI fragment was isolated according to Method 3. 0.5 µg of M13 mp 18 DNA (Pharmacia) was incubated with EcoRI and phosphatase (Method 6). 5 µl of vector DNA were mixed with 5 µl of EcoRI fragment from PK1-B, 2 µl of 10×ligase buffer, 7 µl of water and 1 µl of T4-DNA ligase (6 Weiss units, Pharmacia) and ligated at 14° C. overnight.

The DNA obtained was transformed into *E. coli* TG-1 according to Method 7. A white plaque was picked (Method 8) and used to inoculate 20 ml of LB medium which had been treated with 200 µl of a saturated TG-1 culture. The culture was shaken at 37° C. for 5 hours and the cells were subsequently centrifuged for 5 minutes at 12,000 RM and 4° C. The cells were washed once in water and again centrifuged.

The M13 DNA (MKl-B) was isolated according to Method 10. 50 µl of DNA were digested at 37° C. for 1 hour with 5 units each of Pst I and BamHI and precipitated according to Method 1. The DNA sediment was dissolved in 100 µl of exonuclease III buffer (66 mM Tris/HCl [pH 8.0] 6.6 mM $MgCl_2$). After the addition of 10 µl of exonuclease Ill (Gibco-8RL 5000 units/77 µl ) the mixture was incubated at room temperature for 30 seconds.

After the addition of 10 µl of 0.5M EDTA the sample was inactivated at 65° C. for 10 minutes and precipitated according to method 1. The sediment was dissolved in 50 µl of Sl buffer (2 mM potassium acetate, 1 mM zinc sulphate, 5% (w/v) glycerol) and, after the addition of 10 units of Sl nuclease (Gibco-BRL), incubated at room temperature for 30 minutes. The sample was extracted twice with phenol (Method 6) and the DNA was precipitated (Method 1). The DNA was dissolved in 12 µl of HIN buffer. After the addition of 1 µl of Klenow polymerase (5 units, Pharmacia) the mixture was incubated at room temperature for 2 minutes and, after the addition of 1 µl of 2 mM dATP, dCTP, dGTP, dTTP, again incubated at 37° C. for 2 minutes. 30 µl of water. 5 µl of 10×ligase buffer and 1 µl of T4-DNA ligase (6 Weiss units, Pharmacia) were added and the batch was ligated at 14° C. overnight.

The mixture was transformed into *E. coli* TG-1 (Method 7). 4 white plaques were picked, the DNA was prepared (Method 8) and analyzed by sequencing (Method 9). The DNA used for the expression (see below) was named M2/13. 50 µl of M2/13 DNA were digested completely with 20 units of EcoRI. The DNA was precipitated and dissolved in 50 µl of T4 polymerase buffer. The DNA was digested partially at 37° C. for 2 minutes with 1 unit of HindIII, precipitated (Method 1) and separated on a 0.8% agarose gel (Method 2).

The 1.3 kb DNA EcoRI-HindIII fragment was isolated (Method 3). 50 µl of DNA solution, 6 µl of 10×HIN buffer, 1 µl of Klenow polymerase (5 units, Pharmacia) and 2 µl of 5 mM dATP, dCTP, dGTP, dTTP were mixed and incubated at 37° C. for 30 minutes. The DNA was precipitated (Method 1), resuspended in 10 µl of water and, after the addition of 10 pMoles of a phosphorylated BamHI oligonucleotide adaptor (8-mer: CGGATCCG; New England Biolabs) as well as 2.5 µl of 10×ligase buffer and 6 Weiss units of T4-DNA ligase, ligated at 14° C. overnight. The DNA was precipitated (Method 1) and separated on a 1.0% aragose gel (Method 2). The 1.3 kb DNA fragment was isolated and ligated with 0.1 µg of pDS78/RBSII,6xHis vector as described above. The new plasmid obtained was denoted at p8/3. The nucleotide sequence of this plasmid is shown in FIG. 11.

Further analysis of the clones containing plasmid p8/3 was carried out as described above by SDS protein gels (Method 13) and immunoblots (Method 14). The polypeptide expressed from plasmid p8/3 is a protein having a molecular weight of about 41,000 Dalton. The protein, which is denoted hereinafter as (41 kD), was purified as follows.

2 Purification of the Protein (41 kD) from *E. coli*

60 g of recombinant *E. coli* cells contained p8/3 were disintegrated in two portions each of 30 g for three 1-minute periods in a cell homogenizer (model MSK, Braun, Melsungen, BRD) with in each case 70 g of glass grinding elements (diameter 0.1 mm) and in each case 10 ml of buffer A (50 mM Tris HCl [pH 7.0], 50 mM KCl). The cell material was diluted with 150 ml of buffer A and centrifuged (10,000×g, 30 minutes, 4° C.). The desired protein (41 kD) remained in dissolved form in the supernatant (crude extract).

20 g of Celles P (Bio-Rad) were soaked in buffer A and packed into a column (diameter=5 cm, length=7 cm). After equilibration of the column with buffer A, the crude extract was applied to the column with a pump (throughflow) rate=170 ml/hr.). The absorbed protein (Cellex P eluate) was eluted by increasing the phosphate concentration (gradient with 1M potassium phosphate [pH 7.0]).

Thereafter, the Cellex P eluate was adsorbed on a nickel-nitrilotriacetic acid resin which was produced according to Hochuli et al., J. Chromatogr. 411, 177–184 [1987]. The NTA resin column (diameter=1.6 cm, length=9 cm, throughflow rate=170 ml/hr.) was equilibrated with 0.1M Tris/HCl [pH 7.5], 0.5M NaCl, and the adsorbed protein was eluted (NTA eluate) by means of a gradient of 0 to 0.5M imidazole.

The NTA eluate was concentrated by means of ultrafiltration on a YMIO membrane (Amicon. Div. W.R. Grace & Co., Danvers, Mass., USA) and chromatographed on a Sephacryl ® S-200 column (Pharmacia, diameter=2.6 cm, length=83 cm, throughflow rate=14.6 ml/hr.) in PBS buffer (80 g NaCl, 2 g KCl, 2 g KH2PO4, 29 g Na2HPO4.12 H2O in 10 l of pyrogen-free water). The yield of purified protein was 19 mg (determined according to Lowry, J. Biol. Chem. 193, 265–275 [1951] with BSA as the standard).

3. Immunological and Biochemical Analysis of the Protein

The protein (41 kD), purified as described above, was analyzed by means of polyacrylamide gel electrophoresis and Western blot (Towbin et al., supra) (FIG. 10). Trace 3 (FIG. 10a) shows that the (41 kD) protein was greatly enriched in comparison to the E. coli proteins. In the final product (trace 5), E. coli proteins were no longer visible (FIG. 10b). FIG. 10c shows that the purified protein (41 kD) was present partially as a homodimer. This homodimer formed spontaneously. It could be separated into monomers only partially by treatment with mercaptoethanol.

The amino acid sequence of the protein (41 kD) expressed from plasmid p8/3 corresponded to amino acid sequence (III′″).

By comparing the amino acid sequence of protein (41 kD) with the amino acid sequence of known proteins, it was established that the protein (41 kD) had a strong homology to aldolases. Investigations were therefore carried out to determine whether the purified protein had aldolase activity.

An aldolase colour test was used according to the manufacturer's instructions (SIGMA). The purified protein (41 kD) exhibited a specific activity of 13 μMoles of fructose-1,6-diphosphate per mg of protein per minute at 37° C.

The endotoxin content of the purified protein (41 kD) was determined by means of a LAL test (Pyroquant Diagnostik GmbH, BRD) according to the manufacturer's instructions. An endotoxin content of less than 3.1 EU/mg of protein was measured (EU=endotoxin units).

What is claimed is:

1. A polypeptide which has at least one specific epitope of a *Plasmodium falciparum* merozoite antigen having the amino acid sequence MetAsnAlaProLysLysLeuProAlaAspValAlaGlu-GluLeuAlaThrTrAla-W-LysLeuValGlnAla-GlyLysGlyIleLeuAlaAlaAsp-GluSerThrGlnThrIleLys LysArgPheAspAs-nIleLysLeuGluAsnThrIleGluAsnArgAlaSer-TyrArgAsp LeuLeuPheGlyThrLysGlyLeu-GlyLysPheIleSerGlyAlaIleLeuPheGluGlu ThrLeuPheGlnLysAsnGluAlaGlyValPro-X-ValAsnLeuLeuHisAsnGluAsn IleIlePro-GlyIleLysValAspLys-Y-LeuValAsnIleProCys-ThrAspGluGlu LysSerThrGln-Z-LeuAsp-GlyLeuAlaGluArgCysLysGluTyrTyrLysAlaGly AlaArgPheAlaLysTrpArgThrValLeuValIleAsp-ThrAlaLysGlyLysProThr AspLeuSerAsnHisGlu-ThrAlaTrPGlyLeuAlaArg-TyrAlaSerIleCysGlnGln AsnArgLeuVal-ProIleValGluProGluIleLeuAlaAspGlyProHis-SerIleGlu ValCysAlaValValThrGlnLysVal-LeuSerCysValPheLysAlaLeuGlnGluAsn Gly-ValLeuLeuGluGlyAlaLeuLeuLysProAsnMet-ValThrAlaGlyTyrGluCys ThrAla-LysThrThrThrGlnAspValGlyPheLeuTh-rValArgThrLeuArgArgThr ValProProAlaLeu-ProGlyValValPheLeuSerGlyGlyGlnSerGluGlu-GluAla SerValAsnLeuAsnSerIleAsnAlaLeuGly-ProHisProTrpAlaLeuThrPheSer TyrGlyAr-gAlaLeuGlnAlaSerValLeuAsnThrTrpGln-GlyLysLysGluAsnVal AlaLysAlaArgGluVal-LeuLeuGlnArgAlaGluAlaAsnSerLeuAlaTh-rTyrGly LysTyrLysGlyGlyAlaGlyGlyGluAs-nAlaGlyAlaSerLeuTyrGluLysLysTyr ValTyr wherein —W— is Gln or can be absent;
—X— is Met or Gln;
—Y— is Gly or Cys and
—Z— is Gly or Cys.

2. The polypeptide of claim 1 which has at least one specific epitope of a *Plasmodium falciparum* merozoite antigen having the amino acid sequence MetAsnAlaProLysLysLeuProAlaAspValAlaGlu-GluLeuAlaThrThrAlaLys LeuValGlnAla-GlyLysGlyIleLeuAlaAlaAspGluSerThrGln-ThrIleLysLys ArgPheAspAsnIleLysLeuGluAsn-ThrIleGluAsnArgAlaSerTyrArgAspLeu LeuPhe-GlyThrLysGlyLeuGlyLysPheIleSer-GlyAlaIleLeuPheGluGluThr LeuPheGlnLysAsn-GluAlaGlyValProGlnValAsnLeuLeuHisAsn-GluAsnIle IleProGlyIleLysValAspLysCys-LeuValAsnIleProCysThrAspGluGluLys SerThrGlnGlyLeuAspGlyLeuAlaGluArgCys-LysGluTyrTyrLysAlaGlyAla ArgPheAlaLysT-rpArgThrValLeuValIleAspThrAlaLysGlyLys-ProThrAsp LeuSerAsnHisGluThrAlaTrp-GlyLeuAlaArgTyrAlaSerIleCysGlnGlnAsn Ar-gLeuValProIleValGluProGluIleLeuAlaAspGly-ProHisSerIleGluVal CysAlaValValThrGlnLys-ValLeuSerCysValPheLysAlaLeuGlnGluAsnGly ValLeuLeuGluGlyAlaLeuLeuLysProAsnMet-ValThrAlaGlyTyrGluCysThr Ala-LysThrThrThrGlnAspValGlyPheLeuTh-rValArgThrLeuArgArgThrVal ProProAlaLeu-ProGlyValValPheLeuSerGlyGlyGlnSerGluGlu-GluAlaSer ValAsnLeuAsnSerIleAsnAlaLeuGly-ProHisProTrpAlaLeuThrPheSerTyr GlyAr-gAlaLeuGlnAlaSerValLeuAsnThrTrpGln-GlyLysLysGluAsnValAla LysAlaArgGluVal-LeuLeuGlnArgAlaGluAlaAsnSerLeuAlaTh-rTyrGlyLys TyrLysGlyGlyAlaGlyGlyGluAs-nAlaGlyAlaSerLeuTyrGluLysLysTyrVal Tyr.

3. The polypeptide of claim 1 which has the amino acid sequence

MetArgGlySerHisHisHisHisHisHisGlySerGlyAs-nIleProCysThrAspGlu GluLysSerThrGln-GlyLeuAspGlyLeuAlaGluArgCysLysGluTyr-TyrLysAla GlyAlaArgPheAlaLysTrPArgTh-rValLeuValIleAspThrAlaLysGlyLysPro ThrAs-pLeuSerAsnHisGluThrAlaTrpGlyLeuAlaArg-TyrAlaSerIleCysGln GlnAsnArgLeuVal-ProIleValGluProGluIleLeuAlaAspGlyProHisS-erIle GluValCysAlaValValThrGlnLysVal-LeuSerCysValPheLysAlaLeuGlnGlu Asn-GlyValLeuLeuGluGlyAlaLeuLeuLysProAsn-MetValThrAlaGlyTyrGlu Cys-ThrAlaLysThrThrThrGlnAspValGlyPheLeu-ThraalArgThrLeuArgArg ThrValProProAlaLeu-ProGlyValValPheLeuSerGlyGlyGlnSerGluGlu-Glu AlaSerValAsnLeuAsnSerIleAsnAlaLeuGly-ProHisProTrpAlaLeuThrPhe SerTyrGlyArgAlaLeuGlnAlaSerValLeuAsnThrTrPGln-GlyLysLysGluAsn ValAlaLysAlaArgGluVal-LeuLeuGlnArgAlaGluAlaAsnSerLeuAlaThrTyr GlyLysTyrLysGlyGlyAlaGlyGlyGluAsnAla-GlyAlaSerLeuTyrGluLysLys TyrValTyr.

4. The polypeptide of claim 1 which has the amino acid sequence

MetArgGlySerHisHisHisHisHisHisGlySerGlyAs-nIleProCysThrAspGlu GluLysSerThrGlnCys-LeuAspGlyLeuAlaGluArgCysLysGluTyrTyr-LysAla GlyAlaArgPheAlaLysTrpArgThrVal-LeuValIleAspThrAlaLysGlyLysPro ThrAs-pLeuSerAsnHisGluThrAlaTrpGlyLeuAlaArg-TyrAlaSerIleCysGln GlnAsnArgLeuVal-ProIleValGluProGluIleLeuAlaAspGlyProHis-SerIle GluValCysAlaValValThrGlnLysVal-LeuSerCysValPheLysAlaLeuGlnGlu Asn-GlyValLeuLeuGluGlyAlaLeuLeuLysProAsn-MetValThrAlaGlyTyrGlu Cys-ThrAlaLysThrThrThrGlnAspValGlyPheLeuTh-rValArgThrLeuArgArg ThrValProProAlaLeu-ProGlyValValPheLeuSerGlyGlyGlnSerGluGlu-Glu AlaSerValAsnLeuAsnSerIleAsnAlaLeuGly-ProHisProTrpAlaLeuThrPhe SerTyrGlyAr-gAlaLeuGlnAlaSerValLeuAsnThrTrpGln-GlyLysLysGluAsn ValAlaLysAlaArgGluVal-LeuLeuGlnArgAlaGluAlaAsnSerLeuAlaThrTyr GlyLysTyrLysGlyGlyAlaGlyGlyGluAsnAla-GlyAlaSerLeuTyrGluLysLys TyrValTyr.

5. The polypeptide of claim 1 which has the amino acid sequence

MetArgGlySerHisHisHisHisHisHisGlySer-GluLeuAlaCysGlnTyrMetAsn AlaProLysLys-LeuProAlaAspValAlaGluGluLeuAlaThr-ThrAlaLysLeuVal GlnAlaGlyLys-GlyIleLeuAlaAlaAspGluSerThrGlnThrIleLys-LysArgPhe AspAsnIleLysLeuGluAsnThrIle-GluAsnArgAlaSerTyrArgAspLeuLeuPhe GlyThrLysGlyLeuGlyLysPheIleSer-GlyAlaIleLeuPheGluGluThrLeuPhe GlnLysAsn-GluAlaGlyValProGlnValAsnLeuLeuHisAsn-GluAsnIleIlePro GlyIleLysValAspLysCys-LeuValAsnIleProCysThrAspGluGluLysSerThr GlnGlyLeuAspGlyLeuAlaGluArgCysLys-GluTyrTyrLysAlaGlyAlaArgPhe AlaLysT-rpArgThrValLeuValIleAspThrAlaLysGlyLys-ProThrAspLeuSer AsnHisGluThrAlaTrP-GlyLeuAlaArgTyrAlaSerIleCysGlnGlnAsnAr-gLeu ValProIleValGluProGluIleLeuAlaAspGly-ProHisSerIleGluValCysAla ValValThrGlnLys-ValLeuSerCysValPheLysAlaLeuGlnGluAsn-GlyValLeu LeuGluGlyAlaLeuLeuLysProAsn-MetValThrAlaGlyTyrGuuCysThrAlaLys ThrThrThrGlnAspValGlyPheLeuThrValArgTh-rLeuArgArgThrValProPro AlaLeuProGlyVal-ValPheLeuSerGlyGlyGlnSerGluGluGluAlaSer-ValAsn LeuAsnSerIleAsnAlaLeuGlyProHis-ProTrpAlaLeuThrPheSerTyrGlyArg AlaLeuGl-nAlaSerValLeuAsnThrTrpGlnGlyLysLys-GluAsnValAlaLysAla ArgGluValLeuLeuGlnAr-gAlaGluAlaAsnSerLeuAlaThrTyrGlyLysTyrLys GlyGlyAlaGlyGlyGluAsnAlaGlyAlaSerLeuTyr-GluLysLysTyrValTyr.

6. The polypeptide of claim 1 which has the amino acid sequence

MetArgGlySerHisHisHisHisHisHisGlySer-GluLeuAlaCysGlnTyrMetAsn AlaProLysLys-LeuProAlaAspValAlaGluGluLeuAlaThr-ThrAlaGlnLysLeu ValGlnAlaGlyLys-GlyIleLeuAlaAlaAspGluSerThrGlnThrIleLys-LysArg PheAspAsnIleLysLeuGluAsnThrIle-GluAsnArgAlaSerTyrArgAspLeuLeu Phe-GlyThrLysGlyLeuGlyLysPheIleSer-GlyAlaIleLeuPheGluGluThrLeu PheGlnLysAsn-GluAlaGlyValProGlnValAsnLeuLeuHisAsn-GluAsnIleIle ProGlyIleLysValAspLys-GlyLeuValAsnIleProCysThrAspGluGluLysSer ThrGlnGlyLeuAspGlyLeuAlaGluArgCysLys-GluTyrTyrLysAlaGlyAlaArg PheAlaLysT-rpArgThrValLeuValIleAspThrAlaLysGlyLys-ProThrAspLeu SerAsnHisGluThrAlaTrP-GlyLeuAlaArgTyrAlaSerIleCysGlnGlnAsnArg LeuValProIleValGluProGluIleLeuAlaAspGly-ProHisSerIleGluValCys AlaValValThrGlnLys-ValLeuSerCysValPheLysAlaLeuGlnGluAsnGly-Val LeuLeuGluGlyAlaLeuLeuLysProAsnMet-ValThrAlaGlyTyrGluCysThrAla LysThrThrThrGlnAspValGlyPheLeuTh-rValArgThrLeuArgArgThrValPro ProAlaLeu-ProGlyValValPheLeuSerGlyGlyGlnSerGluGlu-GluAlaSerVal AsnLeuAsnSerIleAsnAlaLeuGly-ProHisProTrPAlaLeuThrPheSerTyrGly ArgAlaLeuGlnAlaSerValLeuAsnThrTrPGln-GlyLysLysGluAsnValAlaLys AlaArgGluVal-LeuLeuGlnArgAlaGluAlaAsnSerLeuAlaThrTyr-GlyLysTyr LysGlyGlyAlaGlyGlyGluAsnAla-GlyAlaSerLeuTyrGluLysLysTyrVal Tyr.

7. The polypeptide of claim 1 which has the amino acid sequence

MetArgGlySerHisHisHisHisHisHisGlySer-GluLeuAlaCysGlnTyrMetAsn AlaProLysLys-LeuProAlaAspValAlaGluGluLeuAlaThr-ThrAlaGlnLysLeu ValGlnAlaGlyLys-GlyIleLeuAlaAlaAspGluSerThrGlnThrIleLy-sLysAr PheAspAsnIleLysLeuGluAsnThrIle-GluAsnArgAlaSerTyrArgAspLeuLeu Phe-GlyThrLysGlyLeuGlyLysPheIleSer-GlyAlaIleLeuPheGluGluThrLeu PheGlnLysAsn-GluAlaGlyValProMetValAsnLeuLeuHisAsn-GluAsnIleIle ProGlyIleLysValAspLys-GlyLeuValAsnIleProCysThrAspGluGluLysSer ThrGlnGlyLeuAspGlyLeuAlaGluArgCysLys-GluTyrTyrLysAlaGlyAlaArg PheAlaLysT-rPArgThrValLeuValIleAspThrAlaLysGlyLys-ProThrAspLeu SerAsnHisGluThrAlaTrP-GlyLeuAlaArgTyrAlaSerIleCysGlnGlnAsnArg LeuValProIleValGluProGluIleLeuAlaAspGly-ProHisSerIleGluValCys AlaValValThrGlnLys-ValLeuSerCysValPheLysAlaLeuGlnGluAsnGly-Val LeuLeuGluGlyAlaLeuLeuLysProAsnMet-ValThrAlaGlyTyrGluCysThrAla LysThrThrThrGlnAspValGlyPheLeuTh-rValArgThrLeuArgArgThrValPro ProAlaLeu-ProGlyValValPheLeuSerGlyGlyGlnSerGluGlu-GluAlaSerVal AsnLeuAsnSerIleAsnAlaLeuGly-proHisProTrpAlaLeuThrPheSerTyrGly Ar-gAlaLeuGlnAlaSerValLeuAsnThrTrpGln-GlyLysLysGluAsnValAlaLys AlaArgGluVal-LeuLeuGlnArgAlaGluAlaAsnSerLeuAlaThrTyr-GlyLysTyr LysGlyGlyAlaGlyGlyGluAsnAla-GlyAlaSerLeuTyrGluLysLysTyrVal Tyr.

8. The polypeptide of claim 1 which has the amino acid sequence

MetArgGlySerHisHisHisHisHisHisGlySer-GluLeuAlaCysGlnTyrMetAsn AlaProLysLys-LeuProAlaAspValAlaGluGluLeuAlaThr-

ThrAlaGlnLysLeu ValGlnAlaGlyLys-GlyIleLeuAlaAlaAspGluSerThrGlnThrIleLys-LysArg PheAspAsnIleLysLeuGluAsnThrIle-GluAsnArgAlaSerTyrArgAspLeuLeu Phe-GlyThrLysGlyLeuGlyLysPheIleSer-GlyAlaIleLeuPheGluGluThrLeu PheGlnLysAsn-GluAlaGlyValProGlnValAsnLeuLeuHisAsn-GluAsnIleIle ProGlyIleLysValAspLys-GlyLeuValAsnIleProCysThrAspGluGluLysSer ThrGlnCysLeuAspGlyLeuAlaGluArgCysLys-GluTyrTyrLysAlaGlyAlaArg PheAlaLysT-rpArgThrValLeuValIleAspThrAlaLysGlyLys-ProThrAspLeu SerAsnHisGluThrAlaTrp-GlyLeuAlaArgTyrAlaSerIleCysGlnGlnAsnArg LeuValProIleValGluProGluIleLeuAlaAspGly-ProHisSerIleGluValCys AlaValValThrGlnLys-ValLeuSerCysValPheLysAlaLeuGlnGluAsnGly-Val LeuLeuGluGlyAlaLeuLeuLysProAsnMet-ValThrAlaGlyTyrGluCysThrAla LysThrThrThrGlnAspValGlyPheLeuTh-rValArgThrLeuArgArgThrValPro ProAlaLeu-ProGlyValValPheLeuSerGlyGlyGlnSerGluGlu-GluAlaSerVal AsnLeuAsnSerIleAsnAlaLeuGly-ProHisProTrpAlaLeuThrPheSerTyrGly Ar-gAlaLeuGlnAlaSerValLeuAsnThrTrpGln-GlyLysLysGluAsnValAlaLys AlaArgGluVal-LeuLeuGlnArgAlaGluAlaAsnSerLeuAlaThrTyr-GlyLysTyr LysGlyGlyAlaGlyGlyGluAsnAla-GlyAlaSerLeuTyrGluLysLysTyrVal Tyr.

9. The polypeptide of claim 1 which has the amino acid sequence

MetArgGlySerHisHisHisHisHisHisGlySer-GluLeuAlaCysGlnTyrMetAsn AlaProLysLys-LeuProAlaAspValAlaGluGluLeuAlaThr-ThrAlaGlnLysLeu ValGlnAlaGlyLys-GlyIleLeuAlaAlaAspGluSerThrGlnThrIleLys-LysArg PheAspAsnIleLysLeuGluAsnThrIle-GluAsnArgAlaSerTyrArgAspLeuLeu Phe-GlyThrLysGlyLeuGlyLysPheIleSer-GlyAlaIleLeuPheGluGluThrLeu PheGlnLysAsn-GluAlaGlyValProMetValAsnLeuLeuHisAsn-GluAsnIleIle ProGlyIleLysValAspLys-GlyLeuValAsnIleProCysThrAspGluGluLysSer ThrGlnCysLeuAspGlyLeuAlaGluArgCysLys-GluTyrTyrLysAlaGlyAlaArg PheAlaLysT-rPArgThrValLeuValIleAspThrAlaLysGlyLys-ProThrAspLeu SerAsnHisGluThrAlaTrP-GlyLeuAlaArgTyrAlaSerIleCysGlnGlnAsnArg LeuValProIleValGluProGluIleLeuAlaAspGly-ProHisSerIleGluValCys AlaValValThrGlnLys-ValLeuSerCysValPheLysAlaLeuGlnGluAsnGly-Val LeuLeuGluGlyAlaLeuLeuLysProAsnMet-ValThrAlaGlyTyrGluCysThrAla LysThrThrThrGlnAspValGlyPheLeuTh-rValArgThrLeuArgArgThrValPro ProAlaLeu-ProGlyValValPheLeuSerGlyGlyGlnSerGluGlu-GluAlaSerVal AsnLeuAsnSerIleAsnAlaLeuGly-ProHisProTrPAlaLeuThrPheSerTyrGly Ar-gAlaLeuGlnAlaSerValLeuAsnThrTrpGln-GlyLysLysGuuAsnValAlaLys AlaArgGluVal-LeuLeuGlnArgAlaGluAlaAsnSerLeuAlaThrTyr-GlyLysTyr LysGlyGlyAlaGlyGlyGluAsnAla-GlyAlaSerLeuTyrGluLysLysTyrVal Tyr.

* * * * *